United States Patent
Auvinen et al.

(10) Patent No.: US 11,850,306 B2
(45) Date of Patent: *Dec. 26, 2023

(54) METHOD FOR DRYING HYDROGEL COMPRISING NANOFIBRILLAR CELLULOSE AND A DRIED HYDROGEL COMPRISING NANOFIBRILLAR CELLULOSE

(71) Applicant: UPM-KYMMENE CORPORATION, Helsinki (FI)

(72) Inventors: Vili-Veli Auvinen, Espoo (FI); Heli Paukkonen, Espoo (FI); Marjo Yliperttula, Espoo (FI); Arto Urtti, Kuopio (FI); Tiina Hakkarainen, Kaavi (FI); Patrick Laurén, Espoo (FI); Mikko Kunnari, Nummela (FI); Timo Laaksonen, Hyvinkää (FI); Mingwei Li, Helsinki (FI); Kari Luukko, Espoo (FI)

(73) Assignee: UPM-KYMMENE CORPORATION, Helsinki (FI)

(*) Notice: Subject to any disclaimer, the term of this patent is extended or adjusted under 35 U.S.C. 154(b) by 92 days.

This patent is subject to a terminal disclaimer.

(21) Appl. No.: 16/468,979

(22) PCT Filed: Dec. 15, 2017

(86) PCT No.: PCT/FI2017/050899
§ 371 (c)(1),
(2) Date: Jun. 12, 2019

(87) PCT Pub. No.: WO2018/109281
PCT Pub. Date: Jun. 21, 2018

(65) Prior Publication Data
US 2020/0078305 A1    Mar. 12, 2020

(30) Foreign Application Priority Data

Dec. 15, 2016 (EP) .................................. 16397537

(51) Int. Cl.
| | |
|---|---|
| *A61K 9/19* | (2006.01) |
| *A61K 47/38* | (2006.01) |
| *A61K 47/10* | (2017.01) |
| *A61K 47/26* | (2006.01) |
| *A61K 9/06* | (2006.01) |
| *A01N 1/02* | (2006.01) |
| *C12N 5/00* | (2006.01) |
| *C12N 5/09* | (2010.01) |
| *F26B 5/06* | (2006.01) |

(52) U.S. Cl.
CPC .............. *A61K 9/19* (2013.01); *A01N 1/0221* (2013.01); *A01N 1/0231* (2013.01); *A61K 9/06* (2013.01); *A61K 47/10* (2013.01); *A61K 47/26* (2013.01); *A61K 47/38* (2013.01); *C12N 5/0062* (2013.01); *C12N 5/0693* (2013.01); *F26B 5/06* (2013.01); *C12N 2513/00* (2013.01); *C12N 2533/78* (2013.01)

(58) Field of Classification Search
CPC . A61K 9/19; A61K 9/06; A61K 47/10; A61K 47/26; A61K 47/38; A61K 9/0014; A61L 26/008; A61L 2400/12; A61L 15/44; A61L 15/28; A61L 26/0023; A01N 1/0231; A01N 1/0221; C12N 5/0062; C12N 2533/78; F26B 5/06
See application file for complete search history.

(56) References Cited

U.S. PATENT DOCUMENTS

| | | |
|---|---|---|
| 6,202,946 B1 | 3/2001 | Virtanen |
| 2009/0130756 A1 | 5/2009 | Klann et al. |
| 2012/0322663 A1 | 12/2012 | Harel et al. |
| 2013/0018112 A1 | 1/2013 | Thielemans et al. |
| 2015/0093560 A1 | 4/2015 | Nemoto et al. |
| 2016/0263228 A1 | 9/2016 | Kluge et al. |
| 2016/0298077 A1 | 10/2016 | Salmons et al. |
| 2016/0325008 A1 | 11/2016 | Laukkanen et al. |
| 2017/0027168 A1 | 2/2017 | Heath |

(Continued)

FOREIGN PATENT DOCUMENTS

| | | |
|---|---|---|
| CN | 103275336 A | 9/2013 |
| CN | 104721145 A | 6/2015 |

(Continued)

OTHER PUBLICATIONS

Valo, H. (2012). Biopolymer-Based Nanoparticles for Drug Delivery.*
Liu et al. Hemicellulose-reinforced nanocellulose hydrogels for wound healing application. Cellulose. 2016;23:3129-3143.*
Hakkarainen et al. Nanofibrillar cellulose wound dressing in skin graft donor site treatment. Journal of Controlled Release. 2016;244:292-301.*
Zepic et al. Morphological, thermal, and structural aspects of dried and redispersed nanofibrillated cellulose (NFC). Holzforschung. 2014;68(6):657-667.*
Prestrelski et al. Separation of Freezing- and Drying-Induced Denaturation of Lyophilized Proteins Using Stress-Specific Stabilization: II. Structural Studies Using Infrared Spectroscopy. Archives of Biochemistry and Biophysics. 1993;303(2):465-473.*

(Continued)

*Primary Examiner* — Lynn Y Fan
(74) *Attorney, Agent, or Firm* — CANTOR COLBURN LLP

(57) ABSTRACT

The present disclosure relates to method for drying hydrogel comprising nanofibrillar cellulose, the method comprising providing a hydrogel comprising nanofibrillar cellulose, providing polyethylene glycol, providing trehalose, mixing the hydrogel, the polyethylene glycol and the trehalose to obtain a mixture, and freeze drying the mixture to obtain a dried hydrogel comprising nanofibrillar cellulose. The present disclosure relates to a freeze-dryable hydrogel comprising nanofibrillar cellulose, to a freeze-dried hydrogel comprising nanofibrillar cellulose, and to a medical hydrogel comprising nanofibrillar cellulose and one or more therapeutic agent(s).

11 Claims, 5 Drawing Sheets

(56) References Cited

U.S. PATENT DOCUMENTS

| | | | |
|---|---|---|---|
| 2019/0343889 A1 | 11/2019 | Luukko et al. | |
| 2021/0127663 A1 | 5/2021 | Paukkonen et al. | |

FOREIGN PATENT DOCUMENTS

| | | | |
|---|---|---|---|
| CN | 104920339 | A | 9/2015 |
| CN | 105254917 | A | 1/2016 |
| CN | 105363070 | A | 3/2016 |
| EP | 2216345 | A1 | 8/2010 |
| JP | 2015105453 | A | 6/2015 |
| JP | 2016094358 | A | 5/2016 |
| WO | 2010102802 | A1 | 9/2010 |
| WO | 2010142850 | A1 | 12/2010 |
| WO | 2013072563 | A1 | 5/2013 |
| WO | 2016097490 | A1 | 6/2016 |

OTHER PUBLICATIONS

International Search Report for International Application No. PCT/FI2017/050899; International Filing Date: Dec. 15, 2017, dated Mar. 27, 2018; 5 pages.

Muller, A. et al., "Bacterial nanocellulose with a shape-memory effect as potential drug delivery system", RSC Advances, vol. 4, 2015; pp. 57173-57184.

Poirier, J.M., "Porous Scaffolds of Cellulose Nanofibres Bound with Crosslinked Chitosan and Gelatine for Cartilage Applications: Processing and Characterization", Master's Thesis, 2013; 52 pages.

Valo, H. et al., "Drug release from nanoparticles embedded in four different nanofibrillar cellulose aerogels", European Journal of Pharmaceutical Sciences, vol. 50, 2013; pp. 69-77.

Written Opinion of the International Searching Authority for International Application No. PCT/FI2017/050899; International Filing Date: Dec. 15, 2017, dated Mar. 27, 2018; 5 pages.

International Search Report for International Application No. PCT/EP2017/071441; International Filing Date: Aug. 25, 2017, dated Aug. 11, 2017; 5 pages.

Nahr, F. K. et al., "Optimization of the nanocellulose based cryoprotective medium to enhance the viability o freeze dried Lactobacillus plantarum using response surface methodology", LWT—Food Science and Technology, vol. 64, 2015; pp. 326-332.

Niu Dan, "The Encapsulation and Vitrification Preservation of a Hydrogel Comprising Human Umbilical Vein Endothelial Cell", University of Science and Technology of China. Chinese Master's Theses Full-text Database: Medicine and Health Sciences; Oct. 15, 2016; 13 pages, with English translation.

Nordli, H. R. et al., "Producing ultrapure wood cellulose nanofibrils and evaluating the cytotoxicity using human skin cells", Carbohydrate Polymers, vol. 150, 2016; pp. 65-73.

Written Opinion of the International Searching Authority for International Application No. PCT/EP2017/071441; International Filing Date: Aug. 25, 2017, dated Aug. 11, 2017; 5 pages.

Cicero, A. L., et al., "Exosomes released by keratinocytes modulate melanocyte pigmentation", Nature Communications; Published Jun. 24, 2015; 8 pages.

U.S. Appl. No. 17/245,445 "A Method for Freeze-Drying a Hydrogel Composition and a Freeze-Dried Hydrogel Composition", filed Apr. 30, 2021.

Fan et al. Recent development in nanocellulose research and application II. Department of Polymer Materials and Engineering. Donghua University. 2010. 21 pages, English Translation.

Jaime et al. Paclitaxel Antibody Conjugates and Trehalose for Preserving the Immunulogical Activity After Freeze- Drying. Current Medicinal Chemistry. No. 4. vol. 11. p. 439-446. English abstract Translation.

Missoum et al. Water Redispersible Dried Nanogibrillated Cellulose by Adding Sodium Chloride. Biomacoromolecules. No. 12. vol. 13. p. 4118-4125. English abstract tranlsation.

Qingdong et al. Research Progress on Improving Dispersion of Nano-Cellulose Particles. Engineering Plastics Application. vol. 41. No. 6. 2013. 4 pages, English abstract translation.

* cited by examiner

A  B

METHOD FOR DRYING HYDROGEL COMPRISING NANOFIBRILLAR CELLULOSE AND A DRIED HYDROGEL COMPRISING NANOFIBRILLAR CELLULOSE

CROSS-REFERENCE TO RELATED APPLICATIONS

This application is a National Stage application of PCT/FI2017/050899, filed Dec. 15, 2017, which claims benefit of European Application No. 16397537.8 filed on Dec. 15, 2016, both of which are incorporated by reference herein in their entirety.

TECHNICAL FIELD

The present disclosure relates to hydrogels comprising nanofibrillar cellulose, which may be used as medical products in medical applications, and to methods for preparing and drying such hydrogels. The medical uses include delivering of therapeutic substances.

BACKGROUND

Nanofibrillar cellulose refers to isolated cellulose fibrils or fibril bundles derived from cellulose raw material. Nanofibrillar cellulose is based on a natural polymer that is abundant in nature. Nanofibrillar cellulose has a capability of forming viscous hydrogel in water.

Nanofibrillar cellulose production techniques are based on grinding of aqueous dispersion of pulp fibers. The concentration of nanofibrillar cellulose in dispersions is typically very low, usually around 0.3-5%. After the grinding or homogenization process, the obtained nanofibrillar cellulose material is a dilute viscoelastic hydrogel.

Because of its nanoscale structure nanofibrillar cellulose has unique properties which enable functionalities which cannot be provided by conventional cellulose. However, for the same reason nanofibrillar cellulose is also a challenging material. For example dewatering or handling of nanofibrillar cellulose may be difficult. Further, after dewatering it is generally difficult to rehydrate or regel the dried material to obtain material having equal properties to the original nanofibrillar cellulose before the dewatering or drying. Especially challenging dewatering process is freeze-drying.

SUMMARY

One embodiment provides a method for drying hydrogel comprising nanofibrillar cellulose, the method comprising
  providing a hydrogel comprising nanofibrillar cellulose,
  providing polyethylene glycol,
  providing trehalose,
  mixing the hydrogel, the polyethylene glycol and the trehalose to obtain a mixture, and
  freeze drying the mixture to obtain a dried hydrogel comprising nanofibrillar cellulose.

One embodiment provides a freeze-dryable hydrogel comprising nanofibrillar cellulose, polyethylene glycol and trehalose.

One embodiment provides a dried hydrogel comprising nanofibrillar cellulose obtained with the method.

One embodiment provides a dried medical hydrogel comprising nanofibrillar cellulose, one or more therapeutic agent(s), polyethylene glycol and trehalose, wherein the moisture content of the hydrogel is 10% or less, preferably in the range of 2-10% (w/w), such as 2-8% (w/w).

The main embodiments are characterized in the independent claims. Various embodiments are disclosed in the dependent claims. The embodiments recited in dependent claims and in the embodiments are mutually freely combinable unless otherwise explicitly stated.

It was surprisingly found out that when using both polyethylene glycol and trehalose in combination as cryoprotectants in the freeze drying process of nanofibrillar cellulose hydrogel it was possible to obtain a dried product, which could be rehydrated or redispersed into a form which restores the original properties of the hydrogel comprising nanofibrillar cellulose, i.e. the dried product can be regelled. Such properties include for example gel properties and controlled release of active pharmaceutical ingredients. The freeze-dried hydrogels comprising nanofibrillar cellulose containing both polyethylene glycol and trehalose regelled to similar homogenous hydrogels as before freeze-drying, while similar freeze-dried hydrogels containing only one of polyethylene glycol or trehalose were regelled as slimy and granular form. The presence of the selected cryoprotectants had no effect to the release profile of the agents from the gels. By drying the hydrogels it is possible to obtain a very long shelf life for medical products. Especially gels containing active agents, such as therapeutic or cosmetic agents, which are unstable at moist conditions, such as proteins and agents sensitive to hydrolysis, can be successfully freeze-dried into forms containing little or practically no water and therefore having a prolonged stability and shelf life. Such freeze-dried medical products may be stored even at room temperature and may be regelled prior to use by adding liquid, such as water or saline. Further, the combination of polyethylene glycol and trehalose prevented precipitation or sedimentation of nanofibrillar cellulose in a solution or dispersion, which effect was not obtained by either of the cryoprotectants alone.

It was also found out that a hydrogel comprising nanofibrillar cellulose could act as a material providing a controllable release of a wide variety of different molecules which could act for example as active therapeutic or cosmetic agents. Nanofibrillar cellulose hydrogel is able to provide a prolonged release of an active agent which effect can be applied to a variety of medical and cosmetic uses. The effect was obtained along a wide range of hydrogel concentrations and for a wide range of releasable molecules of different sizes and types.

Certain advantageous properties of the hydrogel comprising nanofibrillar cellulose include flexibility, elasticity and remouldability. As the hydrogel contains a lot of water, it may also show good permeability. These properties are useful for example when the hydrogel is used as a cover for healing wounds, or in other medical applications, such as for delivering therapeutic or cosmetic agents.

Flexibility is a feature which is desired in many applications, such as in medical applications. For example flexible patches and dressings comprising nanofibrillar cellulose hydrogel are useful for applying onto skin, for example for covering wounds and other damages or injuries, such as burns.

The hydrogels of the embodiments also provide high water retention capacity and molecule diffusion property speed, which properties are desired in medical applications such as wound healing and the like. Large hydrogels may be prepared and/or shaped which may be used for covering large areas.

The hydrogels described herein are useful in medical applications, wherein the materials comprising nanofibrillar cellulose are in contact with living tissue. It was discovered that nanofibrillar cellulose provides unusual properties when it is applied for example onto skin or onto a damaged area. The products containing nanofibrillar cellulose as described herein are highly biocompatible with the living tissue and provide several advantageous effects. Without binding to any specific theory, it is believed that a hydrogel comprising very hydrophilic nanofibrillar cellulose having a very high specific surface area, and thus high water retention ability, when applied against a skin or other tissue, provides favourable moist environment between the tissue or wound and the hydrogel comprising nanofibrillar cellulose. The high amount of free hydroxyl groups in the nanofibrillar cellulose forms hydrogen bonds between the nanofibrillar cellulose and water molecules and enables gel formation and the high water retention ability of the nanofibrillar cellulose. Because of the high amount of water in the nanofibrillar cellulose hydrogel, only water is supposed to be in contact with tissue, and which also enables migration of fluids and/or agents from the skin or wound to the hydrogel, or from the hydrogel to the skin or wound.

When the hydrogels are used for covering wounds or other damages or injuries, for example as such or as part of other products, such as plasters, dressings, medical patches or parts of plasters, patches or dressings, several effects are provided. The usability of the products is good as the product may be applied and removed easily without being damaged, for example torn. When used for covering wounds the hydrogel protects the wound from infection and keeps moist environment for the wound to heal. The hydrogel will not attach to a damaged skin or wound in such irreversible way as conventional materials, which are usually very difficult to remove without damaging the healed area. The conditions between the product and the skin facilitate the healing of a damaged area.

The medical hydrogels of the embodiments are especially advantageous in the treatment of grafts, such as skin graft. The hydrogel may be used for covering the graft area and it acts as a protective layer.

The hydrogels may also be used for controllably and effectively releasing and delivering agents, such as therapeutic or cosmetic agents, to a subject, such as a patient or a user, for example for transdermal route or by other route. The controlled release refers for example to obtaining a desired release rate and/or profile of an agent over a time period, which may be affected by the selection of the gel, for example the percentage of the gel or the thickness of the gel, the concentration or form of the releasable agent(s), presence of any auxiliary agents, or other conditions, such as pH, temperature and the like having an effect to the release rate and/or activity of the releasable agents. The combined effect of the special conditions between the tissue and the hydrogel as explained in previous and the release properties provides efficient delivery of substances into living tissue. The nanofibrillar cellulose hydrogel provides a hydrophilic matrix, which is non-toxic, biocompatible and also biodegradable. For example the matrix may be degraded enzymatically. On the other hand the hydrogel is stable at physiological conditions.

BRIEF DESCRIPTION OF THE DRAWINGS

The embodiments will be explained in the following with reference to the appended drawings, where.

DETAILED DESCRIPTION

Figure 1:
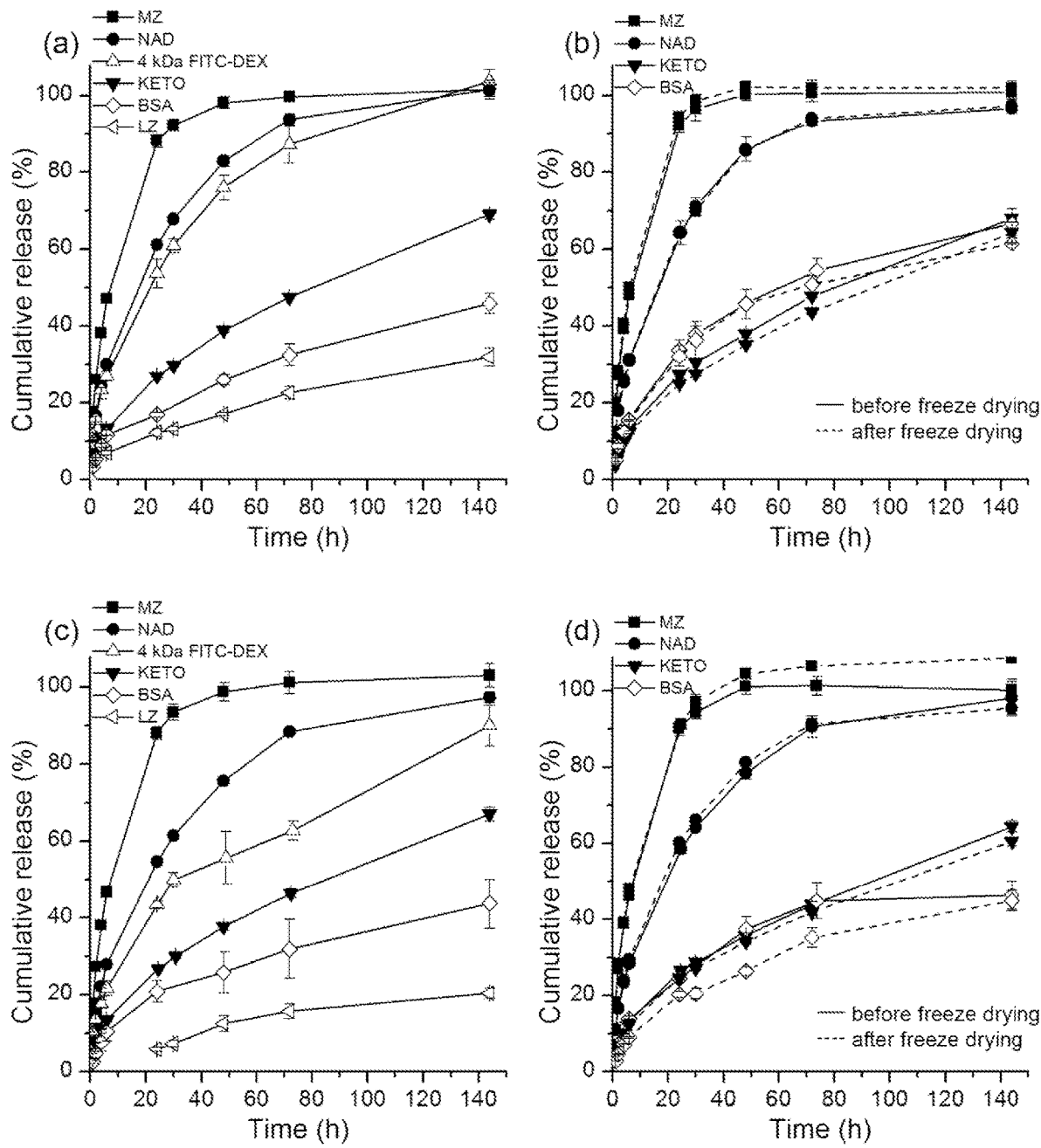
FIG. 1 shows the effect of NFC hydrogel concentration and freeze drying on the release of metronidazole, nadolol, ketoprofen, BSA, lysozyme and 4 kDa FITC-dextran. Formulations contained a) 3% NFC hydrogel combined with metronidazole, nadolol, ketoprofen, BSA, lysozyme or 4 kDa FITC-dextran, b) 3% NFC hydrogel with PEG6000 and trehalose combined with metronidazole, nadolol, ketoprofen or BSA before and after freeze drying, c) 6.5% NFC hydrogel combined with metronidazole, nadolol, ketoprofen, BSA, lysozyme or 4 kDa FITC-dextran, d) 6.5% NFC hydrogel with PEG6000 and trehalose combined with metronidazole, nadolol, ketoprofen or BSA before and after freeze drying. Each curve is the mean±standard deviation of three analyses.

The present disclosure provides hydrogels comprising nanofibrillar cellulose, which may be also called as nanofibrillar cellulose hydrogels. The hydrogels may be provided as products, which may contain also other substances or other elements, such as reinforcing materials, covering materials, active agents, salts or the like. The hydrogels may be also provided or called as medical hydrogels or medical products.

The term "medical" refers to a product or use wherein the product, i.e. a products comprising the hydrogel of the embodiments, is used or is suitable for medical purposes. A medical product may be sterilized, or it is sterilisable, for example by using temperature, pressure, moisture, chemicals, radiation or a combination thereof. The product may be for example autoclaved, or other methods using high temperature may be used, in which cases the product should tolerate high temperatures over 100° C., for example at least 121° C. or 134° C. In one example the product is autoclaved at 121° C. for 15 minutes. It is also desired that a medical product is pyrogen free and it does not contain undesired protein residues or the like. A medical product is preferably non-toxic to the target. Also UV sterilization may be used. A medical product may also be suitable for example for cosmetic purposes.

The nanofibrillar cellulose (NFC) hydrogel of the embodiments, such as anionic NFC hydrogel, is able to controllably release active agents, such as therapeutic agents, for example pharmaceutical ingredients, as a function of time, especially when the temperature and pH are constant. It was found out that NFC hydrogel can be freeze-dried with the specific excipients and still be re-gelled. A research was conducted to investigate, if the lyophilization of NFC hydrogel has any effects on the drug release profiles between a non-freeze-dried and a freeze-dried and re-gelled sample, that are otherwise identical. The results demonstrate that the freeze-drying method with PEG and trehalose together as cryoprotectants has practically no effect on the release capabilities of the used NFC hydrogels, such as anionic hydrogels. Anionic hydrogels are preferred for many applications. For example anionically modified nanofibrillar cellulose does not precipitate easily unlike the other grades. The anionic grade is also especially suitable for releasing certain active agents.

In this specification, percentage values, unless specifically indicated otherwise, are based on weight (w/w). If any numerical ranges are provided, the ranges include also the upper and lower values.

One embodiment provides a freeze-dryable hydrogel comprising nanofibrillar cellulose, polyethylene glycol and trehalose. The polyethylene glycol and trehalose act as cryoprotecting agents providing a synergistic effect, which allows the nanofibrillar hydrogel to be freeze-dried in such way that a freeze-dried product is obtained having substantially identical properties to the hydrogel before the freeze-drying. When polyethylene glycol or trehalose alone were used, they showed no such remarkable cryoprotective effect which could indicate that they would be effective as cryoprotectants for nanofibrillar cellulose hydrogels, or for example prevent precipitation of the nanofibrillar cellulose. Preferably the freeze-dryable hydrogel contains 0.1-2% (w/w) of polyethylene glycol and 0.05-1.0% (w/w) of trehalose calculated from the total mass of the hydrogel.

One embodiment provides a method for drying hydrogel comprising nanofibrillar cellulose, the method comprising
providing a hydrogel comprising nanofibrillar cellulose,
providing polyethylene glycol,
providing trehalose,
mixing the hydrogel, the polyethylene glycol and the trehalose to obtain a mixture, and
freeze drying the mixture to obtain a dried hydrogel comprising nanofibrillar cellulose.

One embodiment provides a medical hydrogel comprising nanofibrillar cellulose and one or more therapeutic agent(s) and/or cosmetic agent(s). The medical hydrogel may be used for administering the agent(s) to a subject. The medical hydrogel may also contain other ingredients, such as polyethylene glycol and trehalose, as described herein. The subject may be a patient or any other subject in need of the agents(s), such as human or animal.

Therefore the main starting material comprises nanofibrillar cellulose, which comprises or consists of cellulose fibrils having diameter in the submicron range. It forms a self-assembled hydrogel network even at low concentrations. These gels of nanofibrillar cellulose are highly shear thinning and pseudoplastic in nature.

Nanofibrillar Cellulose

The nanofibrillar cellulose is prepared normally from cellulose raw material of plant origin. The raw material may be based on any plant material that contains cellulose. The raw material may also be derived from certain bacterial fermentation processes. In one embodiment the plant material is wood. Wood may be from softwood tree such as spruce, pine, fir, larch, douglas-fir or hemlock, or from hardwood tree such as birch, aspen, poplar, alder, eucalyptus, oak, beech or acacia, or from a mixture of softwoods and hardwoods. In one embodiment the nanofibrillar cellulose is obtained from wood pulp. In one embodiment the nanofibrillar cellulose is obtained from hardwood pulp. In one example the hardwood is birch. In one embodiment the nanofibrillar cellulose is obtained from softwood pulp.

The nanofibrillar cellulose is preferably made of plant material. In one example the fibrils are obtained from non-parenchymal plant material. In such case the fibrils may be obtained from secondary cell walls. One abundant source of such cellulose fibrils is wood fibres. The nanofibrillar cellulose is manufactured by homogenizing wood-derived fibrous raw material, which may be chemical pulp. Cellulose fibers are disintegrated to produce fibrils which have the diameter of only some nanometers, which is 50 nm at the most, for example in the range of 1-50 µm, and gives a dispersion of fibrils in water. The fibrils may be reduced to size where the diameter of most of the fibrils is in the range of only 2-20 nm. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging.

As used herein, the term "nanofibrillar cellulose" refers to cellulose fibrils or fibril bundles separated from cellulose-based fiber raw material. These fibrils are characterized by a high aspect ratio (length/diameter): their length may exceed 1 µm, whereas the diameter typically remains smaller than 200 nm. The smallest fibrils are in the scale of so-called elementary fibrils, the diameter being typically in the range of 2-12 nm. The dimensions and size distribution of the fibrils depend on the refining method and efficiency.

Nanofibrillar cellulose may be characterized as a cellulose-based material, in which the median length of particles (fibrils or fibril bundles) is not greater than 50 µm, for example in the range of 1-50 µm, and the particle diameter is smaller than 1 µm, suitably in the range of 2-500 nm. In case of native nanofibrillar cellulose, in one embodiment the average diameter of a fibril is in the range of 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose may also contain small amounts of other wood components, such as hemicellulose or lignin. The amount is dependent on the plant source. Often used parallel names for nanofibrillar cellulose include nanofibrillated cellulose (NFC) and nanocellulose.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low, low viscosity vs. high viscosity etc. The fibrillation technique and the chemical pre-modification have an influence on the fibril size distribution. Typically, non-ionic grades have wider fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood (HW) vs. softwood (SW) pulp, different polysaccharide composition exists in the final nanofibrillar cellulose product. Commonly, the non-ionic grades are prepared from bleached birch pulp, which yields high xylene content (25% by weight). Modified grades are prepared either from HW or SW pulps. In those modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

In an aqueous environment, a dispersion of cellulose nanofibers forms a viscoelastic hydrogel network. The gel is formed at relatively low concentrations of, for example, 0.05-0.2% (w/w) by dispersed and hydrated entangled fibrils. The viscoelasticity of the NFC hydrogel may be characterized, for example, with dynamic oscillatory rheological measurements.

The nanofibrillar cellulose hydrogels exhibit characteristic rheological properties. For example, they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent on the raw material and the disintegration method. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives several successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device, as described in U.S. Pat. No. 6,202,946 B1, includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one embodiment the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The energy taken by the refining work is normally expressed in terms of energy per processed raw material quantity, in units of e.g. kWh/kg, MWh/ton, or units proportional to these. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be, for example, Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used.

The nanofibrillar cellulose provided as a starting material in the method may be characterized by the viscosity it provides in a water solution. The viscosity describes, for example, the fibrillation degree of the nanofibrillar cellulose. In one embodiment the nanofibrillar cellulose when dispersed in water provides a Brookfield viscosity of at least 2000 mPa·s, such as at least 3000 mPa·s, measured at a consistency of 0.8% (w/w) and at 10 rpm. In one embodiment the nanofibrillar cellulose, when dispersed in water, provides a Brookfield viscosity of at least 10000 mPa·s measured at a consistency of 0.8% (w/w) and at 10 rpm. In one embodiment the nanofibrillar cellulose, when dispersed in water, provides a Brookfield viscosity of at least 15000 mPa·s measured at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at a consistency of 0.8% (w/w) and at 10 rpm.

In one embodiment the nanofibrillar cellulose comprises non-modified nanofibrillar cellulose. In one embodiment the nanofibrillar cellulose is non-modified nanofibrillar cellulose. It was found out that the drainage of non-modified nanofibrillar cellulose was significantly faster than with for example anionic grade. Non-modified nanofibrillar cellulose generally has a Brookfield viscosity in the range of 2000-10000 mPa·s, measured at a consistency of 0.8% (w/w) and at 10 rpm.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, that is, pulp.

The modification treatment to the fibers may be chemical or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface. The modification treatment may also be enzymatic.

The cellulose in the fibers may be especially ionically charged after the modification, because the ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. A cationic charge in turn may be created chemically by cationization by attaching a cationic group to the cellulose, such as quaternary ammonium group.

In one embodiment the nanofibrillar cellulose comprises chemically modified nanofibrillar cellulose, such as anionically modified nanofibrillar cellulose or cationically modified nanofibrillar cellulose. In one embodiment the nanofibrillar cellulose is anionically modified nanofibrillar cellulose. In one embodiment the nanofibrillar cellulose is cationically modified nanofibrillar cellulose. In one embodiment the anionically modified nanofibrillar cellulose is oxidized nanofibrillar cellulose. In one embodiment the anionically modified nanofibrillar cellulose is sulphonized nanofibrillar cellulose. In one embodiment the anionically modified nanofibrillar cellulose is carboxymethylated nanofibrillar cellulose. Chemically modified nanofibrillar celluloses may be used to affect to the release profile of certain active agents. For example anionic grades may be used to release cationically charged molecules to obtain a prolonged release rate, or vice versa.

The cellulose may be oxidized. In the oxidation of cellulose, the primary hydroxyl groups of cellulose may be oxidized catalytically by a heterocyclic nitroxyl compound, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

In one embodiment such chemically modified nanofibrillar cellulose, when dispersed in water, provides a Brookfield viscosity of at least 10000 mPa·s measured at a consistency of 0.8% (w/w) and at 10 rpm. In one embodiment such chemically modified nanofibrillar cellulose, when dispersed in water, provides a Brookfield viscosity of at least 15000 mPa·s measured at a consistency of 0.8% (w/w) and at 10 rpm. In one embodiment such chemically modified nanofibrillar cellulose, when dispersed in water, provides a Brookfield viscosity of at least 18000 mPa·s measured at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one embodiment the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at a consistency of 0.8% (w/w) and at 10 rpm.

In one embodiment the nanofibrillar cellulose comprises chemically unmodified nanofibrillar cellulose. In one embodiment such chemically unmodified nanofibrillar cellulose, when dispersed in water, provides a Brookfield viscosity of at least 2000 mPa·s, or at least 3000 mPa·s, measured at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one embodiment said nanofibrillar cellulose has a number average diameter of a fibril in the range of 1-100 nm. In one embodiment said nanofibrillar cellulose has a number average diameter of a fibril in the range of 1-50 nm. In one embodiment said nanofibrillar cellulose has a number average diameter of a fibril in the range of 2-15 nm, such as TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

In one example a rheometer viscosity of the nanofibrillar cellulose dispersion is measured at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s$^{-1}$ is exceeded. This method may be used for determining the zero-shear viscosity.

In one example the nanofibrillar cellulose, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at a consistency of 0.1% (w/w) in aqueous medium, and measured by nephelometry. To characterize the nanofibrillar cellulose these ranges may be combined with the viscosity ranges of the nanofibrillar cellulose, such as nanofibrillar cellulose which, when dispersed in water, provides a Brookfield viscosity of at least 2000 mPa·s, at least 3000 mPa·s, at least 5000 mPa·s, such as at least 10000 mPa·s, for example at least 15000 mPa·s measured at a consistency of 0.8% (w/w) and at 10 rpm.

The starting material for the preparation process is usually nanofibrillar cellulose obtained directly from the disintegration of some of the above-mentioned fibrous raw material and existing at a relatively low concentration homogeneously distributed in water due to the disintegration conditions. The starting material may be an aqueous gel at a concentration of 0.2-10%.

In one embodiment the concentration of the nanofibrillar cellulose in the hydrogel before the freeze-drying is 10% (w/w) or less, less than 10% (w/w), such as in the range of 0.5-10%, 1-10%, such as 2-8% or 1-7%. A preferable range useful for most applications is 3-7%, 4-7% or 4-8%. In the tests the concentrations 3% and 6.5% were selected to represent concentrations near the ends of these ranges. The same concentrations of the hydrogels may be restored after freeze-drying from the freeze-dried gels. More particularly dried gel is redispersable in water and will give, when redispersed in water, for example at a dispergation concentration in the range of 0.1-10% (w/w), such as in the range of 0.5-2.0% (w/w) or 2-8% (w/w) or 3-7% (w/w), a viscosity profile that is equal or substantially equal to the viscosity profile it had originally at the same dispergation concentration.

Polyethylene Glycol

Polyethylene glycol (PEG) is a polyether compound also known as polyethylene oxide (PEO) or polyoxyethylene (POE), depending on its molecular weight. The structure of PEG is commonly expressed as H—(O—CH$_2$—CH$_2$)$_n$—OH. In general polyethylene glycols are prepared by polymerization of ethylene oxide and are commercially available over a wide range of molecular weights from 300 g/mol to 10000000 g/mol. Polyethylene glycol is water-soluble and it has a low toxicity.

In one embodiment the polyethylene glycol has a molecular weight in the range of 100-10000 kDa, such as 1000-10000 kDa. In one embodiment the polyethylene glycol has a molecular weight in the range of 3000-8000 kDa, such as 5000-7000 kDa, for example about 6000 kDa. A "molecular weight" as used in this disclosure may refer to number average molar mass. In general, the number average molecular mass of a polymer can be determined for example by gel permeation chromatography, viscometry via the (Mark-Houwink equation), colligative methods such as vapor pressure osmometry, end-group determination or proton NMR.

Trehalose

Trehalose, also known as α,α-trehalose; α-D-glucopyranosyl-(1→1)-α-D-glucopyranoside, mycose or tremalose, is a natural alpha-linked disaccharide formed by an α,α-1,1-glucoside bond between two α-glucose units. Trehalose is nutritionally equivalent to glucose, because it is rapidly broken down into glucose by the enzyme trehalase. Trehalose may be present as anhydrous or as dihydrate. In one embodiment the trehalose is D(+)-trehalose dehydrate, which is compatible with nanofibrillar cellulose. In one example the trehalose is D-(+)-trehalose dehydrate. It may be provided as solid or as dissolved in an aqueous medium, such as water.

Preparation of the Freeze Dried Product

The method comprises providing the ingredients nanofibrillar cellulose, in general as an aqueous suspension or hydrogel, polyethylene glycol and trehalose. In one embodiment the nanofibrillar cellulose is the only cellulosic material in the aqueous suspension or in the hydrogel. In one embodiment the nanofibrillar cellulose is the only polymeric gel-forming material in the aqueous suspension or in the hydrogel. In one example the aqueous suspension or the hydrogel comprises an amount of another fibrous material, such as non-nanofibrillar cellulose, for example an amount of in the dried hydrogel (w/w) of the dry weight of the fibrous material.

The method comprises providing a hydrogel comprising nanofibrillar cellulose. The concentration of the nanofibrillar cellulose in the hydrogel may be in the range of 0.1-10% (w/w), 0.5-10% (w/w), or 1-10% (w/w), such as 2-8% (w/w). A preferable range useful for most applications is 3-6.5% (w/w), 2.5-7% (w/w), 3-7% (w/w), 4-7% (w/w) or 4-8% (w/w).

The method further comprises mixing the hydrogel, the polyethylene glycol and the trehalose to obtain a mixture. The ingredients may be mixed in any order to obtain an aqueous mixture containing nanofibrillar cellulose, polyethylene glycol and trehalose. In one embodiment the mixture contains 0.1-2% (w/w) of polyethylene glycol and/or 0.05-1.0% (w/w) of trehalose calculated from the total mass of the mixture. In one embodiment the mixture contains 0.2-2% (w/w) of polyethylene glycol and/or 0.1-0.5% (w/w) of trehalose calculated from the total mass of the mixture. In one embodiment the mixture contains 0.5-1.5% (w/w) of polyethylene glycol and/or 0.1-0.5% (w/w) of trehalose calculated from the total mass of the mixture. In one embodiment the mixture contains 0.5-1.5% (w/w) of polyethylene glycol and/or 0.3-0.4% (w/w) of trehalose calculated from the total mass of the mixture. The mixture is in a form of a hydrogel and it may be also called as hydrogel, more particularly a hydrogel comprising nanofibrillar cellulose and preferably other ingredients, such as polyethylene glycol, trehalose and/or other ingredients such as active agents as described herein. In one embodiment the trehalose is present in the range of 5-100 mmol, such as 10-50 mmol, in the mixture. The mixing may be carried out using any suitable mixer or homogenizer, or the ingredients may be mixed by connecting two syringes containing the mixture and injecting the mixture repeatedly between the syringes to obtain mixing and/or homogenization, as was done in the experiments carried out at laboratory scale.

The ratio of dry nanofibrillar cellulose in the gel to the cryoprotectants (NFC:PEG:trehalose by weight) may be for example about 9.5:3:1 to 20:3:1 which ranges were used in experiments. In some examples the ratio of dry nanofibrillar cellulose in the gel to the cryoprotectants (NFC:PEG:trehalose) is in the range of 5-40:2-6:1 by weight, 9-22:2-6:1 by weight, or 9.5-20:2-5:1 by weight, or 9-22:2-4:1 by weight, or 9.5-20:2-4:1 by weight, for example about 10:5:1 by weight or about 10:5:1 by weight, about 15:5:1 by weight, about 10:3:1 by weight, about 15:3:1 by weight or about 20:3:1 by weight.

The obtained mixture is freeze-dryable, i.e. the freeze-drying process does not have remarkable effect to the physical properties of the dried nanofibrillar gel. The mixture may be also called as a freeze-dryable hydrogel. One example of such physical property is a release profile of an agent from the hydrogel, such as small or large molecule(s), for example therapeutic or cosmetic agent(s). It was found out that different molecules having a variety of molecular weights, including relatively small organic molecules as well as larger proteins, could be released from the hydrogel in a controlled way with similar release profile. The useful molecular weight range is very broad, for example in the tests molecules having a molecular weight in the range of about 170-70 000 g/mol (Daltons) could be released controllably. However, the molecules with high molecular weight did release slower than the molecules with lower molecular weight.

In one embodiment the method comprises providing one or more therapeutic agent(s) and mixing the agent(s) with the hydrogel, the polyethylene glycol and the trehalose, i.e. adding the agent(s) to the mixture. The therapeutic agent(s) may be added simultaneously with the polyethylene glycol and/or trehalose, or the therapeutic agents(s) may be added before or afterwards.

In one embodiment the method comprises providing one or more cosmetic agent(s) and mixing the agent(s) with the hydrogel, the polyethylene glycol and the trehalose, i.e. adding the agent(s) to the mixture. The cosmetic agent(s)

may be added simultaneously with the polyethylene glycol and/or trehalose, or the cosmetic agents(s) may be added before or afterwards. A combination of therapeutic agent(s) and cosmetic agent(s) may be also used.

After the mixture has been obtained, it is freeze-dried to obtain a dried hydrogel comprising nanofibrillar cellulose. Any suitable freeze-drying method may be used. Freeze drying, which may also be called as lyophilisation, is a method which uses rapid cooling to produce thermodynamic instability within a system and cause phase separation. The solvent is then removed by sublimation under vacuum leaving behind voids in the regions it previously occupied. Sublimation refers to transition of a substance directly from the solid to the gas phase without passing through the intermediate liquid phase. Sublimation is an endothermic phase transition that occurs at temperatures and pressures below a substance's triple point in its phase diagram.

In one embodiment the freeze drying comprises first lowering the temperature of the mixture to at least to −30° C., such as at least −40° C., for example to the range of −30--100° C., or to the range of −40--100° C., or even to about −200° C. or below, for example when using liquid nitrogen, and after that applying lowered pressure to remove water from the mixture. In general the mixture should be frozen before applying the lowered pressure. In one embodiment the temperature is increased during applying lowered pressure and after applying the lowest pressure, for example the temperature is increased to about −20° C. or even to about −10° C. The temperature may be increased before the lowered pressure is applied, or it may be increased during applying the lowered pressure.

In one example the freeze drying is carried out by freezing the mixture with liquid nitrogen. For example a vial containing the mixture is dipped into liquid nitrogen until the mixture is frozen. After this the lowered pressure is applied to the mixture to remove water from the mixture. The lowered pressure may refer to vacuum required to obtain the sublimation of the water. As the sublimation of the water takes place under the triple point, the required vacuum pressure is dependent on the used temperature.

"Drying" as used herein refers in general to dewatering, which terms may be used interchangeably, wherein water is removed from a hydrogel to obtain dried or dewatered hydrogel. In one embodiment the freeze drying is continued until the hydrogel has a desired moisture content or the freeze drying is continued to a minimum moisture content, preferably below 20%, or more preferably below 10%, or even below 5%, for example to a moisture content in the range of 1-20%, 2-20%, or 2-10% (w/w). In one embodiment the freeze drying is continued until the hydrogel has a moisture content in the range of 2-8%, 2-6%, 2-5% or 1-5% (w/w). In general it may be challenging to obtain a moisture content below 2%. After the low moisture content has been obtained, the dried product may be packed into a package in vacuum or in protective gas. This will prevent the dried hydrogel absorbing the ambient moisture, which might rise the moisture content to a range of for example 4-8%, or 5-7% (w/w). The obtained dried hydrogel may be regelled by adding aqueous liquid, such as water, and suspending the dried product. A regelled or resuspended hydrogel is obtained, which may have the same concentration and water content as before drying. This hydrogel provides characteristics which are substantially equal to the characteristics of the original hydrogel before drying.

Final dried hydrogels, more particularly freeze-dried hydrogels, comprising nanofibrillar cellulose comprising one or more therapeutic agent(s) are obtained with the freeze-drying methods of the embodiments disclosed herein.

One embodiment provides a freeze-dried medical hydrogel comprising nanofibrillar cellulose, one or more therapeutic agent(s), polyethylene glycol and trehalose, wherein the moisture content of the hydrogel is 10% or less (w/w), preferably in the range of 2-10% (w/w), such as 2-8% (w/w), as discussed in the previous.

A freeze-dried hydrogel may be called as an aerogel, more particularly a freeze-dried aerogel. According to one definition, an aerogel is a porous ultralight material derived from a gel, in which the liquid component of the gel has been replaced with a gas. Despite their name, aerogels are solid, rigid, and dry materials that do not resemble a gel in their physical properties: the name comes from the fact that they are made from gels.

One embodiment provides the freeze-dried medical hydrogel, wherein the content of the one or more therapeutic agent in the dried hydrogel in the range of 0.1-65% (w/w), or in the range of 0.1-50% (w/w), such as in the range of 1-25% (w/w), or 1-20% (w/w), 1-10% (w/w), 1-5% (w/w), or 20-65% (w/w), 10-65% (w/w), 5-65% (w/w), 10-50% (w/w), 5-50% (w/w), 5-25% (w/w), 5-20% (w/w), or 5-15% (w/w).

In one embodiment the content of the polyethylene glycol is in the range of 1-10% (w/w) and/or the content of the trehalose is in the range of 0.5-8% (w/w) in the dried hydrogel. In one embodiment the content of the polyethylene glycol is in the range of 5-10% (w/w) and/or the content of the trehalose is in the range of 3-4% (w/w) in the dried hydrogel.

The dried hydrogel may be provided as sheets, blocks or other shapes or forms, in general suitable for the desired medical purpose, and which may be then rewetted before use to obtain a medical gel which is applicable to the target, such as a wound. The dried hydrogel may also be provided as powder or in other crushed form. In such case the method of preparing the product may contain a step of forming the powder, for example by grinding or crushing the freeze-dried product.

The obtained hydrogels, before or after drying, or more particularly after regelling, may be used in variety of applications, such as those described herein, for example in a method for delivering substances to a subject. The hydrogel may be provided for example as a medical product.

Medical Products

The medical products comprising the hydrogel may be used in several applications. One specific field is medical applications, wherein the materials are applied on living tissue, such as skin. The materials may be used in medical products, such as patches, dressings, bandages, filters and the like. The medical products may also be therapeutic products, such as therapeutic patches or gels containing medicament. In general the surface of the product comprising nanofibrillar cellulose will be in contact with the skin during the use. A surface of nanofibrillar cellulose may provide advantageous effects when it is in direct contact with the skin, for example it may promote healing of a wound or other damage on a skin, or it may promote delivery of substances from the medical product to the skin.

The term "wound" as used herein refers to any damages, injuries, diseases, disorders or the like on a tissue, such as skin, mucous membrane, or subcutaneous tissue including tendons, including open or closed wounds, wherein the healing of the wound is desired and may be promoted with the product described herein. The wound may be clean, contaminated, infected or colonized, wherein especially in the latter cases a therapeutic agent, such as an antibiotic, may be administered. Examples of open wounds include abrasions, avulsions, incisions, lacerations, puncture wounds and penetration wounds. Examples of closed wounds include hematomas, crush injuries, sewn wounds, grafts and any skin conditions, diseases or disorders. Examples of conditions, diseases or disorders of the skin include acne, infections, vesiculobullous diseases, cold sore, cutaneous candidiasis, cellulitis, dermatitis and eczema, herpes, hives, lupus, papulosquamous, urticaria and erythema, psoriasis, rosacea, radiation-related disorders, pigmentation, mucinoses keratosis, ulcer, atrophy, and necrobiosis, vasculitis, vitiligo, warts, neutrophilic and eosinophilic diseases, congenital, neoplasms and cancer, such as melanomas and tumours of epidermis or dermis, or other diseases or disorders of epidermis and dermis.

A medical product comprising a therapeutic agent may be provided, wherein the hydrogel comprising nanofibrillar cellulose contain(s) one or more therapeutic agent, such as a bioactive agent, an active agent, a medicament or drug. Also the term pharmaceutical agent may be used interchangeably instead of the term therapeutic agent. Such agents are active or effective agents, which are usually present in effective amounts. The therapeutic agent may be provided in the form of a salt, ester, amide, prodrug, conjugate, active metabolite, isomer, fragment, analog, or the like. The agent may produce a systemic or a local effect in the subject. Such an agent may be provided in a predetermined amount, for example in an amount configured to provide a desired dose of the agent during a certain time period, and/or configured to provide a desired effect on the target, such as skin or other tissue. The content of the therapeutic agent in the product may be for example in the range of 0.01-20% (w/w), such as 0.05-10% (w/w). In one embodiment the content of the therapeutic agent in the product is in the range of 0.1-5% (w/w), such as 0.1-3% (w/w), 0.5-3.5% (w/w) or 0.5-5% (w/w). Especially if the therapeutic agent is included, a controlled, sustained or prolonged release of the agent may be provided. In such case the nanofibrillar cellulose may contain a portion of moisture to enable permeability of the agent. The therapeutic agents may be present in water-soluble form, fat-soluble form or in an emulsion, or in another suitable form.

Examples of therapeutic or bioactive agents which may be administered by using the medical products described herein include proteins, peptides, carbohydrates, lipids, nucleic acids or fragments thereof, preferably as isolated; antibiotics, pain relievers, such as lidocaine; opioids, such as fentanyl or buprenorphine; nicotine; hormones, such as estrogen, contraceptives or androgens, such as testosterone; nitroglycerin; scopolamine; clonidine; antidepressants, such as selegiline; ADHD medication, such as methylphenidate; vitamins, such as B12 or cyanocobalamin; 5-hydroxytryptophan; Alzheimer's medication, such as rivastigmine; acne medication; antipsoriatics, glucocorticoids such as hydrocortisone; antiandrogens such as bifluranol, cyoctol, cyproterone, delmadinone acetate, flutimide, nilutamide and oxendolone; antiestrogens such as delmadinone acetate, ethamoxytriphetol, tamoxifen and toremifene; antimicrobial agents; anesthetics; analgesics; anti-inflammatory compounds or agents; antihistamines; beta-blockers; growth factors; immunomodulators or a medication for treating diseases or disorders of skin. Therapeutic agents may be used for example in medical patches, which may be used on healthy skin or on damaged skin, to provide a prolonged, sustained or extended release of the therapeutic agent from the patch, for example during a period of several hours, for up to 6, 12, 24 or even 48 hours. A bioactive agent is an agent that has an effect on a living organism, tissue or cell.

"Prolonged release", also called as timed release, sustained release or extended release, refers to a drug, or to a carried impregnated with the drug, that is designed to deliver a dose of a medication over an extended period. The aim is to maintain drug concentration within the therapeutic window for maximum or desirable period of time. The terms are generally used in context of oral dosage forms. In addition to pills, capsules and injectable drug carriers (that often have an additional release function), forms of controlled release medicines include gels, implants and devices and transdermal patches. The definition in European Pharmacopoeia recites: "A prolonged-release dosage form is a modified-release dosage form showing a slower release of the active substance(s) than that of a conventional-release dosage form administered by the same route. Prolonged release is achieved by special formulation design and/or manufacturing method. Equivalent term "extended-release dosage form" may be also used.

One embodiment provides the medical product comprising antibiotic agent. Such a product is especially suitable for treating wounds, wherein the wound treating properties are combined with antibiotic properties which prevents infections caused by harmful microbes in the wound. Examples of suitable antibiotics include especially topical antibiotics, such as bacitracin, erythromycin, clindamycin, gentamycin, neomycin, polymyxin, mupirocin, tetracycline, meclocycline, (sodium) sulfacetamide, benzoyl peroxide, and azelaic acid, and combinations thereof. Also other types of antibiotics, such as systemic antibiotics, may be provided, for example penicillins, such as phenoxymethylpenicillin, flucloxacillin and amoxicillin; cephalosporins, such as cefaclor, and cefadroxil; tetracyclines, such as tetracycline, doxycycline and lymecycline; aminoglycosides, such as gentamicin and tobramycin; macrolides, such as erythromycin, azithromycin and clarithromycin; clindamycin; sulphonamides and trimethoprim; metronidazole and tinidazole; quinolones, such as ciprofloxacin, levofloxacin and norfloxacin.

Examples of androgens include boldenone, fluoxymesterone, mestanolone, mesterolone, methandrostenolone, 17-methyltestosterone, 17-alpha-methyltestosterone 3-cyclopentyl enol ether, norethandrolone, normethandrone, Oxandrolone, Oxymesterone, oxymetholone, Prasterone, Stanlolone, Stanozolol, testosterone, testosterone 17-chloral hemiacetal, testosterone 17-beta-cypionate, testosterone enanthate, testosterone nicotinate, testosterone pheynylacetate, testosterone propionate and tiomesterone.

Examples of antibiotics that may be included in the hydrogels include aminoglycosides (e.g., tobramycin, amikacin, gentamicin, kanamycin, netilmicin, tobramycin, streptomycin, azithromycin, clarithromycin, erythromycin, neomycin, erythromycin estolate/ethylsuccinate, gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), cephalosporins (e.g., cephalothin, cefazolin, cefaclor, cefamandole, cefoxitin, cefuroxime, cefonicid, cefinetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin), fluoroquinolones (e.g., ciprofloxacin), carbepenems (e.g., imipenem), tetracyclines (e.g., doxycycline, minocycline, tetracycline), macrolides (e.g., erythromycin and clarithromycin), monobactams (e.g., aztreonam), quinolones (e.g., fleroxacin, nalidixic acid, norfloxacin, ciprofloxacin, ofloxacin, enoxacin, lomefloxacin and cinoxacin), glycopeptides (e.g. vancomycin, teicoplanin), chloramphenicol, clindamycin, trimethoprim, sulfamethoxazole, nitrofurantoin, rifampin and mupirocin, and polymyxins, such as PMB, oxazolidinones, imidazoles (e.g., miconazole, ketoconazole, clotrimazole, econazole, omoconazole, bifonazole, butoconazole, fenticonazole, isoconazole, oxiconazole, sertaconazole, sulconazole and tioconazole), triazoles (e.g., fluconazole, itraconazole, isavuconazole, ravuconazole, posaconazole, voriconazole, terconazole and albaconazole), thiazoles (e.g., abafungin), and allylamines (e.g., terbinafine, naftifine and butenafine), echinocandins (e.g., anidulafungin, caspofunginand micafungin). Other antibiotics can include polygodial, benzoic acid, ciclopirox, tolnaftate, undecylenic acid, flucytosine or 5-fluorocytosine, griseofulvin, and haloprogin.

Antibiotics may be also used for treating acne, for example clindamycin, erythromycin, doxycycline, tetracycline etc. Also other agents may be used, such as benzoyl peroxide, salicylic acid, topical retinoid medicines, such as tretinoin, adapalene or tazarotene, azelaic acid, or androgen blockers such as spirolactone. Psoriasis may be treated for example with steroids, such as corticosteroids, moisturizers, calciprotriene, coal tar, vitamin D, retinoids, tazatorene, anthralin, salicylic acid, methotrexate, or cyclosporine. Insect bites or poison ivy exposure may be treated with agents such as hydrocortisone, emu oil, almond oil, ammonia, bisabolol, papain, diphenylhydramine, jewelweed extract or calamine. Some of these or other treatment agents may be also categorized as cosmetic agents.

Examples of antimicrobial agents that may be included in the hydrogels include silver particles, particularly silver nanoparticles, agents or compounds that release silver ions, chlorhexidine gluconate, and polyhexamethylene biguanide.

Examples of anesthetics that may be included in the hydrogels include procaine, benzocaine, chloroprocaine, cocaine, cyclomethycaine, dimethocaine, piperocaine, propoxycaine, procaine, novocaine, proparacaine, tetracaine, lidocaine, articaine, bupivacaine, cinchocaine, etidocaine, levobupivacaine, mepivacaine, prilocaine, ropivacaine, and trimecaine. In some embodiments, the anesthetic is a combination of lidocaine and prilocaine.

Examples of analgesics that may be included in the hydrogels include opiates and analogues thereof. Exemplary opiates include morphine, codeine, oxycodone, hydrocodone, dihydromorphine, pethidine, buprenorphine, tramadol, fentanyl and venlafaxine.

Examples of anti-inflammatory compounds that may be included in the hydrogels include hydrocortisone, cortisone, dexamethasone, fluocinolone, triamcinolone, medrysone, prednisolone, flurandrenolide, prednisone, halcinonide, methyl prednisolone, prednisone, halcinonide, fludrocortisone, corticosterone, paramethasone, betamethasone, ibuprofen, naproxen, fenoprofen, fenbufen, flurbiprofen, indoprofen, ketoprofen, suprofen, indomethacin, piroxicam, acetosalicylic acid, salicylic acid, diflunisal, methyl salicylate, phenylbutazone, sulindac, mefenamic acid, meclofenamate sodium and tolmetin.

Examples of antihistamines that may be included in the hydrogels include diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine and chlorpheniramine.

Examples of growth factors that may be included in the hydrogels, include vascular endothelial growth factor ("VEGF"), nerve growth factor, such as NGF-beta, platelet derived growth factor (PDGF), fibroblast growth factors, including, for instance, aFGF and bFGF, epidermal growth factor (EGF), keratinocyte growth factor, tumor necrosis factor, transforming growth factors (TGF), including, among others, TGF-alpha and TGF-beta, including TGF-beta-1, TGF-beta-2, TGF-beta-3, TGF-beta-4, or TGF-beta-5, insulin-like growth factors-I and -II (IGF-I and IGF-II), des(1-3)-IGF-I (brain IGF-1), neurotrophin-3 (NT-3) and brain-derived neurotrophic factor (BDNF).

Examples of immunomodulators that may be included in the composition include cyclosporin A, guanylhydrazone, azathioprine, methotrexate, cycphosphamide and tacrolimus.

In some embodiments cells or body fluids are included in the hydrogels. Nanofibrillar cellulose is not toxic to cells, so cells may be for example grown, transferred, dried and/or frozen in the nanofibrillar cellulose hydrogel. One embodiment provides a medical hydrogel comprising nanofibrillar cellulose and one or more cell(s) or cell types, preferably isolated cells. One embodiment provides a medical hydrogel comprising nanofibrillar cellulose and a body fluid, such as one or more type of isolated body fluid.

The cells may be prokaryotic or eukaryotic cells. For example microbial cells may be included, such as bacterial cells or yeast cells. Eukaryotic cells may be plant cells or animal cells. Cells may be cultured cells. Examples of eukaryotic cells include transplantable cells, such as stem cells, for example omnipotent, pluripotent, multipotent, oligopotent or unipotent cells. In case of human embryonic stem cells the cells may be from a deposited cell line or made from unfertilized eggs, i.e. "parthenote" eggs or from parthenogenetically activated ovum, so that no human embryos are destroyed. The cells may be cultured in the hydrogel, and they may be also freeze-dried in it. The cells can be maintained and proliferated on or in the hydrogel without animal or human based chemicals originating outside the cells. The cells may be evenly dispersed on or in the hydrogel.

Examples of cells include stem cells, undifferentiated cells, precursor cells, as well as fully differentiated cells and combinations thereof. In some examples the cells comprise cell types selected from the group consisting of keratocytes, keratinocytes, fibroblast cells, epithelial cells and combinations thereof. In some examples the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells and combinations thereof.

The body fluids, which may be also called as bodily fluids or biofluids, are liquids originating from inside the bodies of living organisms, for example humans or animals. They include fluids that are excreted or secreted from the body, and body water that normally is not. Examples of body fluids include amniotic fluid, aqueous humour and vitreous humour, bile, blood serum, breast milk, cerebrospinal fluid, cerumen (earwax), chyle, chime, endolymph and perilymph, exudates, feces, female ejaculate, gastric acid, gastric juice, lymph, mucus such as nasal drainage and phlegm, pericardial fluid, peritoneal fluid, pleural fluid, pus, rheum, saliva, sebum (skin oil), serous fluid, semen, smegma, sputum, synovial fluid, sweat, tears, urine, vaginal secretion and vomit. They may be also divided into intracellular fluids and extracellular fluids, such as intravascular fluids, interstitial fluids, lymphatic fluids, and transcellular fluids. Also plant fluids may be included, such as plant exudates.

One embodiment provides a medical product, such as a dressing, a patch or a filter, comprising the hydrogel described herein.

The freeze-dried hydrogel described herein may be provided as an implant, or as any other suitable medical device, for example a delivery device, configured to be introduced or implanted into a body of a subject, such as a patient or any other subject in the need thereof. The implant comprising the freeze-dried medical hydrogel may be introduced within tissue, a body lumen, or other location such that the hydrogel is exposed to bodily fluids or other aqueous environment. The implant may have a surface area in the range of 10-1000 $mm^2$, for example in the range of 300-600 $mm^2$. The implant may have a suitable size and shape, for example cylindrical shape. In one example the length of a cylindrical implant is in the range of 5-60 mm, and the diameter is in the range of 1.5-5 mm. The implant may be hydrated or wetted prior implanting, or it may be arranged to be hydrated in the body after implanted.

One embodiment provides the hydrogel for use for treating and/or covering skin wounds or other damages. One embodiment provides such a hydrogel for use as a dressing or a patch, or in a dressing or a patch, for treating and/or covering skin wounds or other damages.

One embodiment provides the hydrogel for use for treating and/or covering skin wounds covered with a graft, such as a skin graft. One embodiment provides the hydrogel for use as a dressing or a patch, or in a dressing or a patch, for treating and/or covering skin wounds covered with a graft, such as a skin graft.

One embodiment provides the hydrogel for use for administering a therapeutic agent, more particularly one or more therapeutic agent(s). In one example the hydrogel may be provided as such or for example in a patch. In one example the hydrogel may be provided in injectable form. One or more therapeutic agent(s) may be included, for example impregnated, in the hydrogel as described herein, and the administration to a patient may be for example dermal, transdermal or subcutaneous.

One embodiment provides a cosmetic product, such as a dressing, a mask or a patch, comprising the hydrogel. Such a product may be called also as a cosmetic product. The product may be provided in various shapes, for example a mask may be designed to fit onto face, for example below eye or onto chin, nose or forehead. One embodiment provides the hydrogel for use as a cosmetic product. The product may be used for releasing one or more cosmetic agent(s) to the user, such as to the skin of the user. Such a cosmetic product may comprise one or more cosmetic agent(s). Cosmetic agent(s) may be included, for example impregnated, in the product wherefrom they will be released or delivered. The content of a cosmetic agent in the product may be for example in the range of 0.01-20% (w/w), such as 0.05-10% (w/w). In one embodiment the content of the cosmetic agent in the product is in the range of 0.1-5% (w/w), such as 0.1-3% (w/w), or 0.5-5% (w/w). The cosmetic agents may be present or provided in the product similarly as explained above for therapeutic agents, and vice versa. The cosmetic use may be analogous to medical use described herein, especially the administering of therapeutic agent. Cosmetic agents may be used also for cosmetically treating skin diseases or disorders, such as those mentioned herein. Such cosmetic products may be used for example for treating pimples, acneic skin, brown sports, wrinkles, oily skin, dry skin, aged skin, spider veins, after sun erythemas, black circles etc. Examples of cosmetic patches include skin cleansers, such as pore cleansers, blackhead removers, stretching stripes, short-term patch-like masks, short-term treatment patches and overnight treatment patches.

Examples of cosmetic agents include forms of vitamins and precursors thereof, such as vitamin A; for example retinoids, such as retinaldehyde (retinal), retinoic acid, retinyl palmitate and retinyl retinoate, ascorbic acid, alpha-hydroxy acids such as glycolic acid and lactic acid; glycols; biotechnology products; keratolytics; amino acids; antimicrobials; moisturizers; pigments; antioxidants; plant extracts; cleansing agents or make-up removers; anti-cellulite agents such as caffeine, carnitine, *Ginkgo biloba* and horse-chestnut; conditioners; fragrances such as aromatherapy agents and perfumes; humectants such as urea, hyaluronic acid, lactic acid and glycerine; emollients such as lanolin, triglycerides and fatty acid esters; FR scavengers, singlet oxygen scavengers, superoxide scavengers or hydrogen peroxide scavengers, such as ascorbic acid (vitamin C), glutathione, tocopherol (vitamin E), carotenoids, coenzyme Q10, bilirubin, lipoic acid, uric acid, enzyme mimetic agents, idebenone, polyphenols, selenium, spin traps such as phenyl butyl nitrone (PBN), protein methionine groups, superoxide dismutase, catalase, selenium peroxidases, heme oxygenases etc. or combinations thereof. The cosmetic agents may be present in water-soluble form, fat-soluble form or in an emulsion, or in another suitable form.

The medical or cosmetic hydrogels as described herein may be provided as incorporated or packed in an application device, such as a syringe, an applicator, a pump or a tube containing the desired amount of the hydrogel, such as syringes of the size from 0.5 ml to 200 ml or even more. The device may comprise a mouthpiece or nozzle providing constant flow of the hydrogel in desired thickness and breadth and geometrics. In one example the hydrogel is in an injectable form having a concentration and viscosity in such range that enables the injection, for example though a needle or through the syringe mouthpiece or nozzle. A freeze-fried hydrogel may be provided as packed in a sealed package, for example in vacuum package or a package containing protective gas. The hydrogel may be, especially in the freeze-dried form, in a form of an implant, which may be for example a medical capsule, or the like. These "ready for use" devices may be packed, sterilized and stored, and used when desired. These application devices may be incorporated in ready-to use kits. The moisture content of the freeze-dried hydrogel, or the product containing thereof, such as a product comprising therapeutic agent, may be in the range of 1-10% (w/w), such as in the range of 2-8% (w/w), 1-5% (w/w), 2-5% (w/w), or 5-7% (w/w). In one example such as package is provided with a separate container containing liquid, such as water, saline solution, buffer solution or the like aqueous liquid in a predetermined amount arranged to rehydrate the gel into a desired moisture content, as described herein. The liquid may be provided for example in a syringe or the like applicator, or a package may contain a separate compartment for the liquid which may be connected to another compartment containing the dried hydrogel, for example by pressing the package and breaking a seal or the like to cause the liquid and the dried gel to be in contact with each other. The liquid may be also applied with other methods, such as by soaking the dried gel in a container containing the liquid. After applying the liquid to the dried gel, a regelled hydrogel comprising nanofibrillar cellulose, polyethylene glycol and trehalose and optionally the therapeutic and/or cosmetic agent(s) is obtained.

One embodiment provides a method for cosmetically treating skin, the method comprising applying the medical product or the cosmetic product described herein onto skin.

One embodiment provides the medical product or the cosmetic product described herein packed in a separate packing. Separate packings may be provided as a series of packings. Usually such packed products are provided as sterilized.

One embodiment provides a kit comprising the medical product or the cosmetic product described herein, for example a packed product, wherein the kit may contain one or more of the packed products. The kit may also contain other materials or equipment, such as a container containing water or other aqueous solution, such as saline solution or the like, for pretreating the product(s) prior to use, for example a predetermined amount of water or other aqueous solution for obtaining a desired moisture content of the re-gelled product.

One example provides a method for delivering or administering substances to a subject, the method comprising providing the medical hydrogel as described in the embodiments containing one or more substance(s), such as therapeutic or cosmetic substance(s) or agent(s), and applying the hydrogel onto skin of the subject. The subject may be a patient or any other subject in need of the substance(s), such as human or animal. By applying the hydrogel onto the skin, the substance(s) will be delivered transdermally, preferably by controlled and/or prolonged release rate.

One example provides a method for delivering substances to a subject, the method comprising providing the medical hydrogel, as described in the embodiments, containing one or more substance(s), such as therapeutic or cosmetic substance(s) or agent(s), and injecting the hydrogel to the subject. The injection, or more precisely the administration route, may be subcutaneous or intramuscular.

One example provides a method for treating skin wounds or other damages or injuries, the method comprising applying the medical product described herein onto the wound, damage, or injury. One specific example provides a method for treating skin wounds covered with a graft, such as a skin graft, for example a mesh graft or a full thickness graft, the method comprising applying the medical product described herein onto the graft.

Grafting refers to a surgical procedure to move tissue from one site to another on the body, or from another person, without bringing its own blood supply with it. Instead, a new blood supply grows in after it is placed. Autografts and isografts are usually not considered as foreign and, therefore, do not elicit rejection. Allografts and xenografts are recognized as foreign by the recipient and are rejected.

Skin grafting is often used to treat skin loss due to a wound, burn, infection, or surgery. In the case of damaged skin, it is removed, and new skin is grafted in its place. Skin grafting can reduce the course of treatment and hospitalization needed, and can also improve function and appearance. There are two types of skin grafts: Split-thickness skin grafts (epidermis+part of the dermis) and full-thickness skin grafts (epidermis+entire thickness of the dermis).

A mesh graft is a full- or partial-thickness sheet of skin that has been fenestrated to allow drainage and expansion. Mesh grafts are useful in many locations on the body because they conform to uneven surfaces. They can be placed in locations that have excessive motion because they can be sutured to the underlying wound bed. Additionally, their fenestrations provide outlets for fluid that may accumulate beneath the graft, which helps reduce tension and the risk of infection and improve vascularization of the graft.

Before applying the medical product onto skin the product may be pretreated i.e. moisture or wetted, in general with an aqueous solution. The moisturizing or wetting may be carried out for example by using water or regular physiological saline solution, which is usually a solution of 0.90% w/w of NaCl, having an osmolality of about 308 mOsm/l. Other types of aqueous solutions may also be used, such as saline solutions with different concentrations. Moisturizing or wetting the material enhances contact with the skin and the moldability of a sheet of material.

Examples

Lyophilization and Re-Gelling of Nanofibrillious Cellulose Hydrogel with Active Pharmaceutical Ingredients (API)

As evidenced by the following examples it was found out that the freeze-drying process does not influence the drug release properties of the NFC hydrogel. Therefore, the API's are released from the freeze-dried (and re-gelled) NFC hydrogel with a similar profile as from the original NFC hydrogel.

The chosen API's for the experiments were Metronidazole, Nadolol, BSA (bovine serum albumin), and ketoprofen due to their different physiochemical properties. The procedures used for each API and NFC hydrogel mixture was the same.

The weighted amounts of API's, cryoprotectants and NFC gels are presented in the Table 1.

TABLE 1

| Fiber % | NFC (g) | Trehalose (mg) | PEG 6000 (mg) | API | m(API) (mg) | NFC dry content (mg) | Gel total mass (mg) incl API + additives | NFC % (w/w) | Trehalose % (w/w) | PEG 6000 % (w/w) | API % (w/w) |
|---|---|---|---|---|---|---|---|---|---|---|---|
| 3.0 | 4.44 | 15 | 45 | Metronidatzole | 90 | 142.08 | 4590 | 3.10 | 0.33 | 0.98 | 1.96 |
| 3.0 | 4.44 | 15 | 45 | Nadolol | 76.5 | 142.08 | 4576.5 | 3.10 | 0.33 | 0.98 | 1.67 |
| 3.0 | 4.44 | 15 | 45 | BSA | 45 | 142.08 | 4545 | 3.13 | 0.33 | 0.99 | 0.99 |
| 3.0 | 4.44 | 15 | 45 | Ketoprofen | 157.5 | 142.08 | 4657.5 | 3.05 | 0.32 | 0.97 | 3.38 |
| 6.5 | 4.44 | 15 | 45 | Metronidatzole | 90 | 301.92 | 4590 | 6.58 | 0.33 | 0.98 | 1.96 |
| 6.5 | 4.44 | 15 | 45 | Nadolol | 76.5 | 301.92 | 4576.5 | 6.60 | 0.33 | 0.98 | 1.67 |
| 6.5 | 4.44 | 15 | 45 | BSA | 45 | 301.92 | 4545 | 6.64 | 0.33 | 0.99 | 0.99 |
| 6.5 | 4.44 | 15 | 45 | Ketoprofen | 157.5 | 301.92 | 4657.5 | 6.48 | 0.32 | 0.97 | 3.38 |

The samples were freeze-dried and the structure of the freeze-dried samples were studied by microscopy. The dried materials were re-gelled and the diffusion properties of the obtained re-gelled hydrogels were studied.

The Release Studies of Small Molecules and Protein Size Model Compounds from the Anionic NFC-Hydrogels
Objectives and Background of the Study The objective was to study how the NFC hydrogel concentration and processing degree affect the release profiles of different molecular weight FITC-dextran, proteins and small molecules, with different charges, from the hydrogel formulations. According to a hypothesis the amount of NFC fibers and the processing degree should alter the release profiles of compounds with a high molecular weight (>1 kDA) from the hydrogels. For small molecules, the objective was to study whether the different charge of the model compound affects the release profile or not. Two different hydrogel grades were tested of TEMPO oxidized NFC hydrogels with the model compounds in the diffusion studies. Specifically, 3.0% and 6.5% TEMPO oxidized NFC hydrogel concentrations with processing degree of 3 were used.

The model compounds in the release studies included small molecules with molecular weight below 500 M metronidazole, nadolol and ketoprofen. These molecules have different charges in pH 7.4. 4 kDa FITC-dextran, lysozyme and bovine serum albumin (BSA) represent high molecular weight compounds in our study. FITC-dextran and proteins were selected based on their molecular weight to demonstrate the diffusion of larger molecules with possible linearity in relation to the hydrodynamic radius of the compounds.

Permeation of small molecules and proteins though hydrogels is affected by their size, shape, charge and relative hydrophilic and hydrophobic character. Also the availability of free water molecules to hydrate and dissolve the solute molecules in addition to hydrogel pore size, pore size distribution and the pore interconnections affect the diffusion rate of molecules through the hydrogel. The main release mechanism of small molecules and proteins from hydrogels can be characterized by Fickian diffusion. The diffusion rate of solutes may be influenced through weak interactions such as electrostatic, hydrophobic and hydrogen bonding between the hydrogel polymer network and solutes.

In the second part of the study an additional objective was to study the effect of freeze drying of the NFC hydrogel on the performance of the formulations.

Dissolution profiles of selected model compounds were evaluated prior to and after freeze drying with excipients. The freeze dried aerogel formulations were hydrated and dispersed to their original concentrations in order to form the original hydrogel structure prior to the dissolution testing. Thermal analysis was performed to the freeze dried aerogel formulations with differential scanning calorimetry (DSC) and thermogravimetric analysis (TGA) in order to evaluate the compatibility of formulations components and residual moisture content. Also viscosity measurements for the formulations were performed before and after freeze drying to evaluate the effect of freeze drying on the rheological properties of the hydrogel formulations. Re-agglomeration and hornification are typical disadvantages during the drying process of NFC. One object was to minimize these phenomenas by adding cryoprotectant excipients, trehalose and PEG 6000, into the formulations. The morphology of the aerogels was evaluated with scanning electron microscopy (SEM). Confocal microscopy was used in the imaging of the hydrated NFC hydrogels.

Materials

TEMPO oxidized nanofibrillar cellulose hydrogels 3.0% and 6.5% were provided by UPM and used as received. All model compounds and reagents were of analytical grade. Bio-Rad Protein Assay reagent was purchased from Bio-Rad, USA. 4 kDa FITC-dextran was purchased from Sigma-Aldrich, Sweden. D-(+)-trehalose dihydrate was purchased from Sigma-Aldrich, USA. Metronidazole was purchased from Sigma-Aldrich, China. Nadolol was purchased from Sigma-Aldrich, Finland. Ketoprofen was purchased from Orion pharma, Finland. Lysozyme from hen egg white was purchased from Roche, Germany. Polyethylene glycol 6000 was purchased from Fluka, Switzerland. Dulbecco's Phosphate Buffered Saline (10×) concentrate without calcium and magnesium was purchased from Gibco, UK. Acetonitrile was of analytical grade.

Methods

Preparation of the Formulations with Oxidized NFC Hydrogels and Model Compounds:

Model compound containing NFC hydrogel formulations were prepared in 10 ml syringes with homogenization mixing for 10 min in the syringes (FIG. 5). 4 kDa FITC-dextran was added into the NFC hydrogel from 1 mg/ml stock solution with a 1% final concentration of FITC-dextran in the NFC hydrogel. Metronidazole, nadolol and ketoprofen were added as dry powders into the NFC hydrogel with final concentrations of 2% for metronidazole, 1.7% for nadolol and 3.4% for ketoprofen. BSA and lysozyme were also added as dry powders into the NFC hydrogels with final concentrations of 1% BSA and 0.5% lysozyme. For metronidazole, nadolol and ketoprofen excess amount of drug was used in relation to the solubility in pH 7 and therefore the drug containing NFC hydrogel formulations were monolithic dispersions. With 4 kDa FITC-dextran, BSA and lysozyme formulations were prepared with NFC hydrogel where the amount of drug did not exceed the solubility limit in pH 7 and therefore these formulations were monolithic solutions.

In Vitro Release Studies:

In vitro drug release studies were performed with modified intrinsic dissolution disc dies filled with 1.07 g of formulations with a constant flat surface area of 1.33 $cm^2$. Discs were placed in 150 ml amber glass vessels on top of a holder. The vessels were filled to a final volume of 70 ml with pH 7.4 phosphate buffered saline (1×DPBS) and kept at 37° C. under constant magnetic stirring (400 rpm) on top of a multi-position magnetic stirrer IKA RT10 (IKA-Werke GmbH & Co KG, Germany). 1.5 ml samples were collected from the vessels and replaced with fresh buffer at 1, 2, 4, 6, 24, 30, 48, 72 and 144 h. All experiments were done in triplicate.

Quantification of Model Compounds from In Vitro Release Samples:

Ketoprofen and nadolol concentrations from the in vitro release samples were analyzed with Ultra performance liquid chromatography (UPLC) instrument Acquity UPLC (Waters, USA). For ketoprofen, the used column was HSS-C18 1.8 μm (2.1×50 mm) (Waters, USA) at 30° C. The flow rate was 0.5 ml/min and the injection volume 5 μl. The ketoprofen detection was performed at 255 nm wavelength. During the gradient run the mobile phase consisted of a mixture of acetonitrile and 15 mM phosphate buffer pH 2 in 25:75 ratio at 0-3 min. After 3 min the mobile phase composition was changed to 75:25 ratio. The retention time of ketoprofen was 1.69 min. The linear concentration of ketoprofen was established in the range of 0.1-25 μg/ml and LOQ for ketoprofen was 0.03 μg/ml. For nadolol, the used column was HSS-T3 1.8 μm (2.1×50 mm) (Waters, USA) at 30° C. The flow rate was 0.5 ml/min and the injection volume 5 μl. The nadolol detection was performed at 215 nm wavelength. During the gradient run the mobile phase consisted of a mixture of acetonitrile and 15 mM phosphate buffer pH 2 in 10:90 ratio at 0-3 min. After 3 min the mobile phase composition was changed to 50:50 ratio. The retention time of nadolol was 0.92 min. The linear concentration of nadolol was established in the range of 0.1-50 µg/ml and LOQ for nadolol was 0.1 µg/ml.

FITC-dextran quantification was performed by fluorescence intensity measurements with an automated multimode plate reader Varioskan Flash (Thermo Fisher Scientific, Finland). 200 µl of samples were pipetted into wells of 96-well OptiPlate plates (PerkinElmer, Finland). Excitation wavelength 490 nm, emission wavelength 520 nm and 12 nm bandwidth were used. The established linear range for FITC-dextran calibration curves was 0.005-0.15 µg/ml with squared correlation coefficients above 0.99 (R>0.99).

Metronidazole and lysozyme quantification was performed by spectrophotometric analysis with Cary 100 UV-Vis spectrophotometer (Varian Inc., USA). For metronidazole, absorbance was measured in 1 cm cell at 320 nm with 12 nm bandwidth against blank. The established linear range for metronidazole calibration curve was 3-35 µg/ml with squared correlation coefficient above 0.99 (R>0.99). For lysozyme, absorbance was measured in 1 cm cell at 280 nm with 12 nm bandwidth against blank. The established linear range for lysozyme calibration curve was 1-17 µg/ml with squared correlation coefficient above 0.99 (R>0.99).

BSA quantification was performed by colorimetric Bio-Rad protein assay, which is based on Bradford dye-binding method. Shortly, 150 µl of each BSA standard sample and BSA sample was pipetted in triplicate into separate microtiter well plates and 50 µl of diluted Bradford dye reagent was added. Sample and reagent were mixed thoroughly with a multi-channel pipet and incubated for 20 minutes at room temperature before absorbance measurement. Absorbance was measured with a well plate reader Varioskan Flash ((Thermo Fisher Scientific, Finland) at 470 nm and 595 nm with 5 nm bandwidth. The established linear range for BSA calibration curves was 1-40 µg/ml with squared correlation coefficients above 0.99 (R>0.99). Linearization of the assay was used to improve accuracy and sensitivity.

Results

Figure 2:
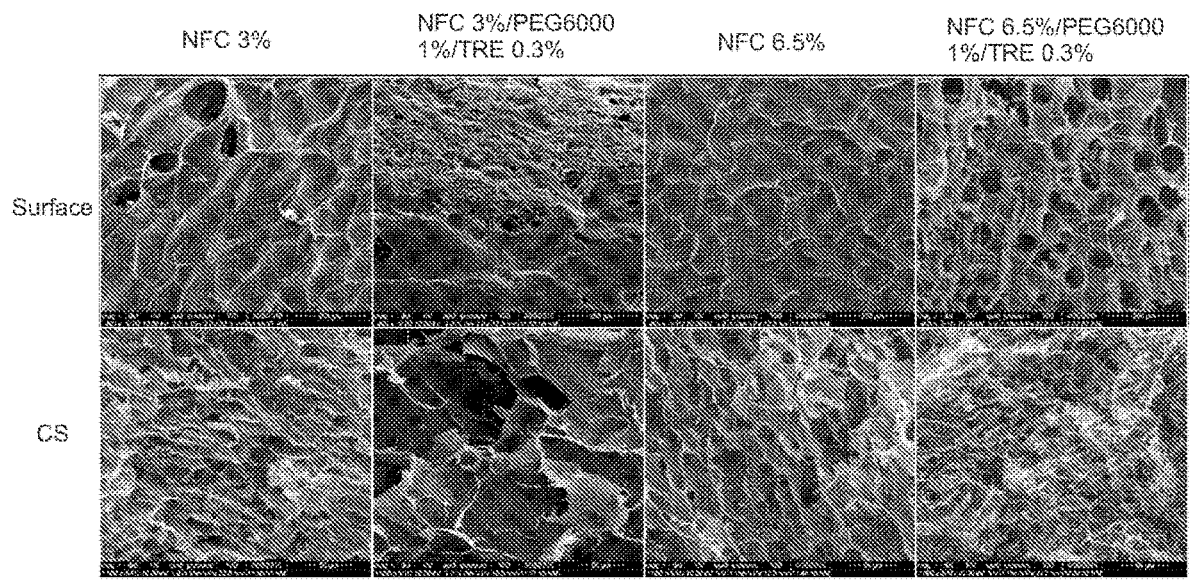
FIG. 2 shows SEM micrographs of freeze dried highly porous NFC aerogels. 3% and 6.5% NFC freeze dried with and without trehalose and PEG6000. Scale bar is 200 μm for top row (surface) and 50 μm for lower row (cross section).

Cumulative in vitro release profiles of the model compounds from different NFC hydrogel formulations are presented in FIG. 1. Table 2 summarizes physicochemical parameters, aqueous solubility values and diffusion coefficients of the model compounds. Mathematical equations were used for the modelling of diffusion controlled drug release that take into consideration structure of the device, the ratio of initial drug concentration to drug solubility and the device geometry. The diffusion coefficients were calculated by Higuchi equation (1) for small molecules with a presumption that these systems could be described as monolithic dispersions (Equations 1 and 2 below). For large molecules (1 kDa) equations we used to solve Fick's second law of diffusion and diffusion coefficients (2) with a presumption that these systems could be described as monolithic solutions (FIG. 2).

$$M_t = A\sqrt{Dc_s(2c_{ini} - c_s)t} \tag{1}$$

$$\frac{M_t}{M_\infty} \leq 0.6 \quad \Rightarrow \quad \frac{M_t}{M_\infty} = 4\left(\frac{Dt}{\pi L^2}\right)^{\frac{1}{2}}$$

$$\frac{M_t}{M_\infty} = 1 - \frac{8}{\pi^2}\sum_{n=0}^{\infty}\frac{\exp[-D(2n+1)^2\pi^2 t/L^2]}{(2n+1)}$$

$$\frac{M_t}{M_\infty} \geq 0.4 \quad \Rightarrow \quad \frac{M_t}{M_\infty} = 1 - \frac{8}{\pi^2}\exp\left(-\frac{\pi^2 Dt}{L^2}\right) \tag{2}$$

Table 2. Physicochemical parameters of model compounds BSA, lysozyme, FITC-dextran, metronidazole, ketoprofen and nadolol. Literature values for intrinsic solubility and solubility in pH 7 are included. Calculated values of diffusion coefficients for model compounds from different NFC hydrogels are presented.

| Compound | Molecular weight (g/mol) | Solubility in aqueous media (mg/ml) | pKa/pI | Charge at pH 7.0 | Hydrodynamic diameter (nm) | Diffusion coefficient in NFC-hydrogels ($10^{-8}$ cm$^2$/s) | | | |
|---|---|---|---|---|---|---|---|---|---|
| | | | | | | 11804-3 (3.2%) | 11814-1 (5.7%) | 11814-3 (5.7%) | 11815-3 (6.8%) |
| BSA | $6.65 \times 10^4$ | 40 | 4.6-4.8 | − | ~7 | 9.28 (±2.46) | 13.93 (±3.42) | 14.34 (±2.56) | 9.06 (±1.16) |
| Lysozyme | $1.47 \times 10^4$ | >10 | 11.1 | + | ~3.7 | 3.53 (±0.31) | 1.79 (±0.52) | 2.57 (±0.10) | 1.75 (±0.15) |
| FITC-dextran | 4000 | 50 | | ø | ~2.8 | 59.44 (±11.23) | 40.03 (±3.73) | 47.52 (±7.95) | 40.01 (±4.84) |
| Metronidazole | 171 | 10.5 (25° C.), 10.5 (pH 7) | 2.38 | ø | | 716.99 | 609.51 | 551.09 | 617.51 |
| Ketoprofen | 254 | 0.107 (25° C.), 6.36 (pH 7) | 4.06 | − | | 152.62 | 131.41 | 148.23 | 141.86 |
| Nadolol | 309 | 8.3 (25° C.), 8.3 (pH 7) | 9.28 | + | | 286.24 | 273.21 | 287.50 | 230.62 |

For small molecules metronidazole, ketoprofen and nadolol the effect of charge seemed to have a weak impact on the cumulative release profiles in pH 7.4 (FIG. 1). Metronidazole was in the neutral form and had the highest diffusion coefficient values followed by cationic nadolol and anionic ketoprofen (Table 2). For hydrophilic metronidazole and nadolol it was found out that the charge of the molecule may have affected the drug release profile as neutral metronidazole diffused faster from NFC hydrogels when compared to cationic nadolol. The surface of TEMPO oxidized NFC is negatively charged and therefore the electrostatic interaction with cationic nadolol may have been more pronounced than with neutral metronidazole hence resulting in slower drug release. Furthermore, solubility of the compounds may have influenced the drug release profiles in a greater extent than the charge of the molecules. This phenomena was observed as prolonged drug release rate for anionic ketoprofen which based on solely charge should have had faster drug release rate than cationic nadolol. The NFC hydrogel concentration had an impact on the cumulative release profiles as well as diffusion coefficients of all small molecules. Overall, the processing degree of the NFC hydrogel had minimal impact on the cumulative drug release profiles of the small model compounds. For small molecules the diffusion coefficients were slightly smaller when higher NFC fiber content was present in the formulations indicating that the amount of NFC fibers in the formulation can be used to control the drug release rate. The concentration of NFC fibers in the formulations had a higher impact on the release profiles of the model compounds than the processing degree.

For large model compounds BSA, lysozyme and FITC-dextran charge had a significant impact on the cumulative release profiles in pH 7.4 (FIG. 1). Neutral FITC-dextran had the highest diffusion coefficient values followed by anionic BSA and cationic lysozyme (Table 2). These results indicate that for large molecules the charge of the molecule was more significant than the molar mass for an impact on the cumulative release profile. Cationic lysozyme had the smallest diffusion coefficient values and overall most prolonged release profile. By contrast, anionic BSA had higher diffusion coefficient values. The molar mass of BSA is higher than the molar mass of lysozyme and therefore the charge of these molecules has clearly affected the cumulative release profiles in a greater extent than the effect of molecule size on the diffusion rate. The NFC hydrogel concentration had an impact on the cumulative release profiles as well as diffusion coefficients of all large model compounds. Overall, the processing degree of the NFC hydrogel had minimal impact on the cumulative release profiles of the large model compounds. For large molecules the diffusion coefficients were significantly smaller when higher NFC fiber content was present in the formulations indicating that the amount of NFC fibers in the formulation can be used to control the drug release rate. The concentration of NFC fibers in the formulations had a higher impact on the release profiles of the large model compounds than the processing degree.

Conclusions

Based on the results the effect of molecule charge and the consequent electrostatic interaction of molecules with the surface of negatively charged TEMPO oxidized NFC fibers was clearly observed for large 1 kDa) model compounds in the in vitro release studies. For small molecules the effect of molecule charge on the release profiles was not as pronounced as for large model compounds. Therefore, it was found out that for small molecules the charge of the molecule is not as significant as for large molecules when the diffusion rate from the NFC hydrogels is evaluated. Overall, the diffusion of small molecules from the NFC hydrogels was faster than the diffusion of large model compounds when solubility had minimal impact. For large model compounds the diffusion rate from NFC hydrogel network was slower due to the size as well as charge of these compounds when compared to small molecules. The NFC hydrogel concentration had an impact on the release profile of small molecules as well large model compounds. Therefore, the NFC fiber concentration in the hydrogel can be used to control the release rate of small as well as large molecule size pharmaceutical compounds. However, the effect of NFC concentration on the release rates of large molecule size compounds is more affected than for small molecules. Finally, it was observed that the concentration of NFC fibers in the formulations had a higher impact on the release profiles of the model compounds than the processing degree.

Freeze Drying of NFC Hydrogel Formulations

One part of the study focus on the freeze drying of NFC hydrogel formulations described below. Morphology, residual moisture content and thermal behaviour of the freeze dried aerogels were evaluated. Drug release properties before and after freeze drying process were evaluated. Rheological properties before and after freeze drying were evaluated as described below.

Polyethylene glycol and trehalose were chosen as cryoprotectants because of the synergistic effect detected especially at the redispersing phase. NFC hydrogels containing only polyethylene glycol, only trehalose, and both polyethylene glycol and trehalose as cryoprotectants were prepared and freeze-dried. Water was added to all samples in similar way, but only the hydrogels containing both polyethylene glycol and trehalose were regelled into proper gel form, i.e. into similar form as before freeze-drying. This could be detected immediately by visual examination. No sedimentation of the hydrogel was detected. The hydrogel samples containing only polyethylene glycol or only trehalose did not regel into homogenous gel form but the result was slimy and granular, which was not suitable material for further studies. Further, when the samples were left into glass bottles overnight, the hydrogel sedimented and a clearly visible water phase was separated in the bottles containing no cryoprotectants or only polyethylene glycol or only trehalose, but not in the ones containing both polyethylene glycol and trehalose.

Figure 7:
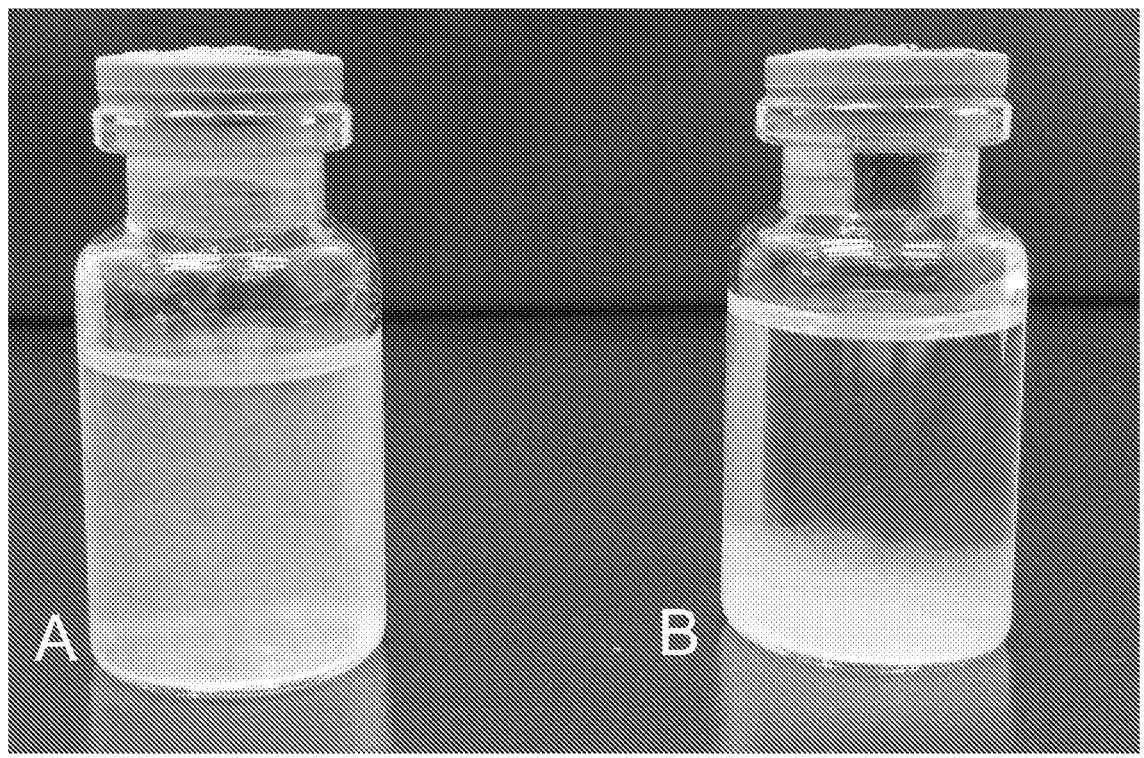
FIG. 7 shows redispersed NFC hydrogels after overnight stay in room temperature: A) with polyethylene glycol and trehalose, B) without polyethylene glycol and trehalose

FIG. 7 shows the effect of the cryoprotectants polyethylene glycol and trehalose to redispersed NFC hydrogels after being incubated overnight at room temperature in a glass bottle (A). Without polyethylene glycol and trehalose (B) the NFC hydrogel was completely sedimented to the bottom of the bottle. Similar sedimentation was also observed when only polyethylene glycol or only trehalose was used.

Key findings of the studies indicate:

The potential of TEMPO oxidized NFC hydrogel at high concentrations, 3% and 6.5%, for controlled drug release applications were evaluated. Most formulation studies have previously focused on the use of more dilute NFC grades. The use of highly concentrated NFC hydrogels in this regard can be considered novel.

It was discovered and shown that TEMPO oxidized NFC hydrogel can be successfully freeze dried and redispersed into a hydrogel form. The used cryoprotectants, PEG6000 and trehalose, together significantly improved the storage and loss modulus of the rehydrated and redispersed NFC hydrogels after freeze drying as opposed to formulations without these cryoprotectants. The viscosity of the freeze dried NFC hydrogels with excipients was also preserved upon rehydration.

These finding indicate that cryoprotectants aided in preserving the structure of the NFC fibers during the freeze drying process. The production of NFC aerogels therefore did not significantly alter rheological properties. Furthermore, the drug release profiles of the model compounds were similar before and after freeze drying. This is a highly desirable feature for API formulations as the shelf-life of the product can be increased by the dry state of aerogel for otherwise hydrolysis sensitive APIs. The aerogels can be easily rehydrated and administered upon need.

Materials and Methods 2.1. Materials

TEMPO oxidized nanofibrillar cellulose hydrogels 3.0% and 6.5% were provided by UPM-Kymmene Corporation, Finland. All model compounds and reagents were of analytical grade. Bio-Rad Protein Assay reagent was purchased from Bio-Rad, USA. 4 kDa FITC-dextran was purchased from Sigma-Aldrich, Sweden. D-(+)-trehalose dihydrate was purchased from Sigma-Aldrich, USA. Metronidazole was purchased from Sigma-Aldrich, China. Nadolol was purchased from Sigma-Aldrich, Finland. Ketoprofen was purchased from Orion Pharma, Finland. Lysozyme from hen egg white was purchased from Roche, Germany. Polyethylene glycol 6000 was purchased from Fluka, Switzerland. Dulbecco's Phosphate Buffered Saline (10×) concentrate without calcium and magnesium was purchased from Gibco, UK. Acetonitrile was of analytical grade, Sigma-Aldrich, Germany.

2.2. Methods—Phase I-III

Preparation of the NFC Hydrogel Formulations

Figure 5:
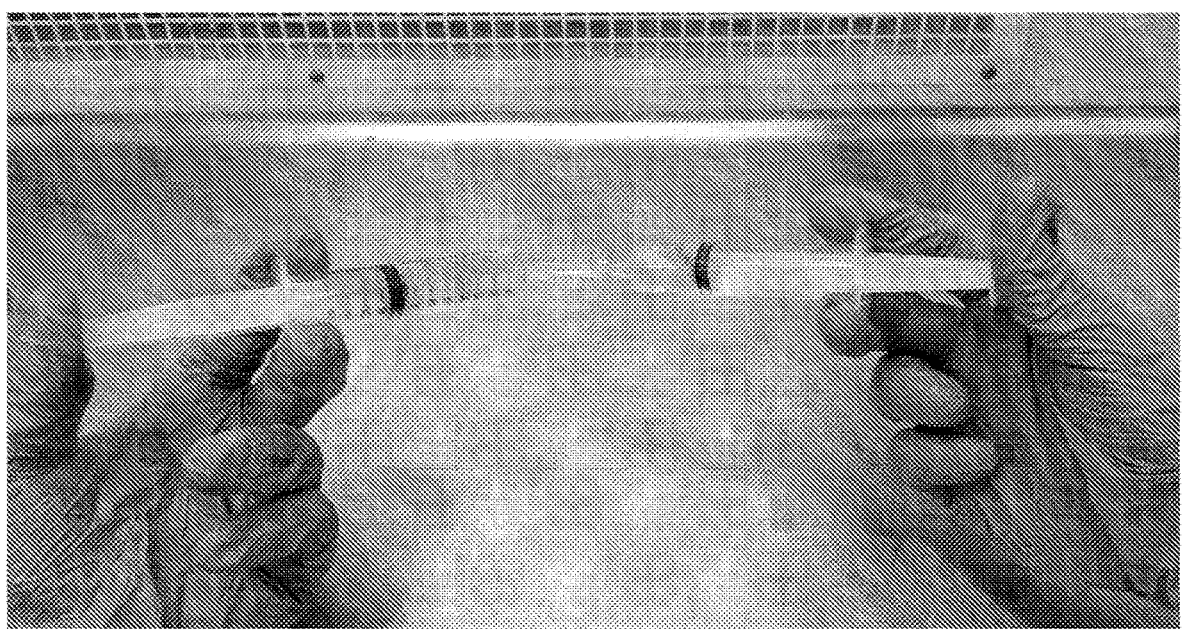
FIG. 5 shows gel mixing by connecting two syringes. Each gel was mixed for 10 minutes.

NFC hydrogel formulations were prepared in 10 ml syringes with homogenization mixing for 10 min in the syringes (FIG. 5). Table 3 contains formulation compositions of NFC hydrogel and model compound physical mixtures. 4 kDa FITC-dextran was added into the NFC hydrogel from 1 mg/ml stock solution with a 1% final concentration of FITC-dextran in the NFC hydrogel. Metronidazole, nadolol and ketoprofen were added as dry powders into the NFC hydrogel with final concentrations of 2% for metronidazole, 1.7% for nadolol and 3.4% for ketoprofen. BSA and lysozyme were added as dry powders into the NFC hydrogels with final concentrations of 1% BSA and 0.5% lysozyme. For metronidazole, nadolol and ketoprofen we used excess amount of drug in relation to the solubility in pH 7 and therefore the drug containing NFC hydrogel formulations were monolithic dispersions. With 4 kDa FITC-dextran, BSA and lysozyme we prepared formulations with NFC hydrogel where the amount of drug did not exceed the solubility limit in pH 7 and therefore these formulations were monolithic solutions.

TABLE 3

Physical mixtures of NFC hydrogel and model compounds.

| API | NFC % (w/w) | API % (w/w) |
|---|---|---|
| Metronidazole | 3 | 2 |
| Nadolol | 3 | 1.7 |
| BSA | 3 | 1 |
| Ketoprofen | 3 | 3.4 |
| Lysozyme | 3 | 0.5 |
| 4 kDa FITC-dextran | 3 | 1 |
| Metronidazole | 6.5 | 2 |
| Nadolol | 6.5 | 1.7 |
| BSA | 6.5 | 1 |
| Ketoprofen | 6.5 | 3.4 |
| Lysozyme | 6.5 | 0.5 |
| 4 kDa FITC-dextran | 6.5 | 1 |

NFC hydrogel formulations of metronidazole, nadolol, ketoprofen and BSA were prepared with PEG6000 and trehalose (Table 4). These formulations were prepared for the evaluation of drug release properties prior to and after freeze drying of the formulations. PEG6000 and trehalose were added to the formulations to perform as cryoprotectants against hornification and re-agglomeration of NFC. Freeze dried aerogels of metronidazole, nadolol, ketoprofen and BSA containing formulations were rehydrated gravimetrically. These hydrogels were then redispersed by homogenization mixing in the syringes for 10 min.

TABLE 4

Formulation compositions for freeze dried aerogels.

| API | NFC % | Trehalose % | PEG 6000 | API % |
|---|---|---|---|---|
| Metronidazole | 3 | 0.3 | 1 | 2 |
| Nadolol | 3 | 0.3 | 1 | 1.7 |
| BSA | 3 | 0.3 | 1 | 1 |
| Ketoprofen | 3 | 0.3 | 1 | 3.4 |
| Metronidazole | 6.5 | 0.3 | 1 | 2 |
| Nadolol | 6.5 | 0.3 | 1 | 1.7 |
| BSA | 6.5 | 0.3 | 1 | 1 |
| Ketoprofen | 6.5 | 0.3 | 1 | 3.4 |

Freeze Drying Protocol

Figure 6:
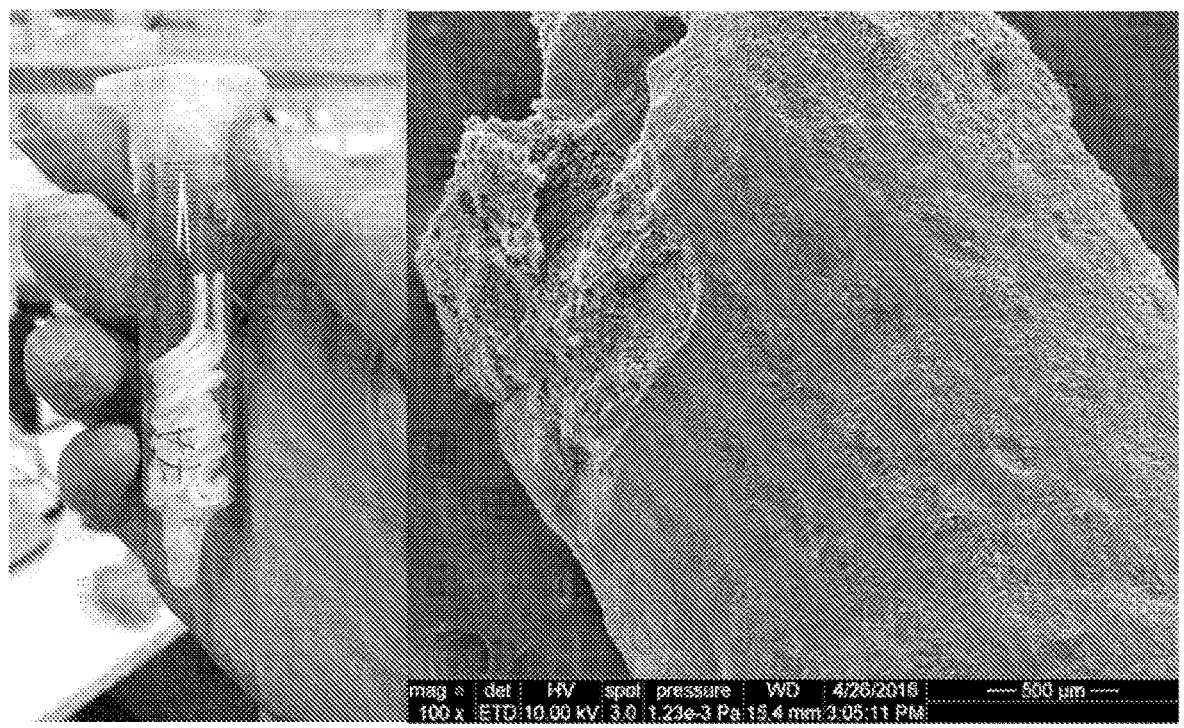
FIG. 6 shows A) a freeze-dried nadolol gel protected by parafilm and B) a SEM image of freeze-dried nadolol gel.

NFC hydrogels and NFC hydrogel formulations with model compounds and cryoprotectants were used for aerogel preparation using the freeze drying process. 2.5 ml of each type of NFC hydrogel and hydrogel formulation were placed inside 10 ml syringes after which these hydrogels were quickly frozen by dipping the hydrogel in liquid nitrogen for 1 minute. The frozen samples were immediately transferred to a freeze dryer (FreeZone 2.5, LabConco, USA) and freeze dried in vacuum (70 mTorr) at a sublimating temperature of −52° C. for 29 h. The final freeze dried samples were sealed in syringes and stored inside a silica desiccator until used. FIG. 6A shows a freeze-dried nadolol gel protected by parafilm.

Scanning Electron Microscopy (SEM)

Figure 3:
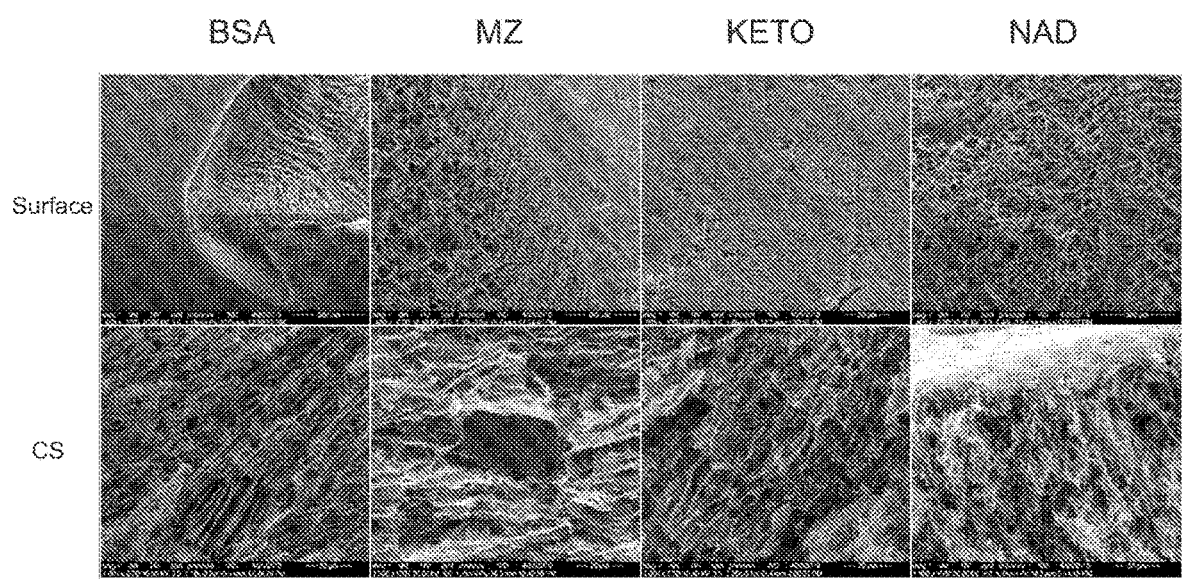
FIG. 3 shows SEM micrographs of freeze dried 3% NFC aerogels containing 1% BSA, 2% metronidazole (MZ), 3.4% ketoprofen (KETO) and 1.7% nadolol (NAD) from left to right. Scale bar is 200 μm for top row (surface) and 50 μm for lower row (cross section).

The morphology of the freeze dried aerogels was imaged with a scanning electron microscope Quanta FEG250 (SEM, FEI Company, USA). The aerogels were fractured manually for analysis of the inner aerogel structure or cut with a scalpel for the analysis of the aerogel surface structure. Micrographs of the cross-sections as well as surface structures of the aerogels were obtained. Before imaging the samples were fixed onto a two-sided carbon tape and sputtered with platinum for 25 s with an Agar sputter device (Agar Scientific Ltd., UK). SEM images are presented in FIGS. 2, 3, and 6B. FIG. 2 shows SEM micrographs of freeze dried highly porous 3% and 6.5% NFC aerogels with and without trehalose and PEG6000 on surfaces of the gels and on cross-sections (CS). FIG. 3 shows similar SEM micrographs of freeze dried 3% NFC aerogels with 1% PEG6000 and 0.3% trehalose and containing 1% BSA, 2% metronidazole (MZ), 3.4% ketoprofen (KETO) and 1.7% nadolol (NAD) from left to right.

Thermogravimetry Analysis (TGA)

The residual moisture content of the aerogels was determined using TGA (TGA 850, Mettler-Toledo, Switzerland). Samples were heated from 25 to 240° C. at a heating rate of 10° C./min in nitrogen (40 ml/min) atmosphere. Residual moisture content of the aerogels was determined as a mass loss (%) of evaporated water.

Differential Scanning Calorimetry (DSC)—Supplementary Data

Thermal analysis of the freeze dried NFC aerogels and model compounds were carried out using a differential scanning calorimeter Mettler Toledo DSC 823e (Mettler Toledo, Giessen, Germany). The samples were placed in sealed aluminum pans with closed lids and heated at a scanning rate of 10° C./min between 25 and 200° C. in nitrogen atmosphere. The data was analyzed with STARe software (Mettler-Toledo, Giessen, Germany).

Rheological Measurements

The rheological measurements were performed at 37° C. with HAAKE Viscotester iQ Rheometer (Thermo Fisher Scientific, Karlsruhe, Germany) equipped with a Peltier system for temperature control. Results were analyzed with HAAKE RheoWin 4.0 software (Thermo Fisher Scientific). Parallel 35 mm diameter steel plate-and-plate geometry was used with a 1 mm gap in all measurements. Before each measurement, the samples were allowed to rest for 5 min at 37° C. Controlled stress amplitude sweeps were performed to determine the linear viscoelastic region for different NFC hydrogel formulations. Constant angular frequency ω=1 Hz and oscillatory stress between 0.0001-500 Pa was used in all amplitude sweeps. The chosen oscillatory stresses for frequency sweeps were τ=50 Pa (3% NFC hydrogel), τ=80 Pa (5.7% NFC hydrogel) and τ=100 Pa (6.5% NFC hydrogel) and the angular frequency range was 0.6-125.7 rads$^{-1}$. Shear viscosity was measured by increasing the shear rate from 0.1 to 1000 1/s.

The used settings in the rheology measurements were as follows
  Amplitude: CS mode
  shear stress amplitude sweep, 37° C., t=300 s hold→osc amp sweep, τ=0.0001-500 Pa, f=1 Hz (6.2832 rad/s) log, 16 steps
  Frequency: CS mode
  frequency sweep with constant shear stress, 37° C., t=300 s hold,
  τ=50 Pa (3.2%), T=80 Pa (5.7%) and τ=100 Pa (6.8%)
  f=0.1 Hz-20 Hz (eli ω=0.6283 rad/s-125.7 rad/s)
  log, 16 steps
  Viscosity: CR mode
  shear rate (1/s)=0.1-1000

In Vitro Release Studies:

In vitro drug release studies were performed with modified intrinsic dissolution disc dies filled with 1.07 g of formulations with a constant flat surface area of 1.33 cm2. Discs were placed in 150 ml amber glass vessels on top of a holder. The vessels were filled to a final volume of 70 ml with pH 7.4 phosphate buffered saline (1×DPBS) and kept at 37° C. under constant magnetic stirring (400 rpm) on top of a multi-position magnetic stirrer IKA RT10 (IKA-Werke GmbH & Co KG, Germany). 1.5 ml samples were collected from the vessels and replaced with fresh buffer at 1, 2, 4, 6, 24, 30, 48, 72 and 144 h. All experiments were done in triplicate.

Quantification of Model Compounds from In Vitro Release Samples

Ketoprofen and nadolol concentrations from the in vitro release samples were analyzed with Ultra performance liquid chromatography (UPLC) instrument Acquity UPLC (Waters, USA). For ketoprofen, the used column was HSS-C18 1.8 µm (2.1×50 mm) (Waters, USA) at 30° C. The flow rate was 0.5 ml/min and the injection volume 5 µl. The ketoprofen detection was performed at 255 nm wavelength. During the gradient run the mobile phase consisted of a mixture of acetonitrile and 15 mM phosphate buffer pH 2 in 25:75 ratio at 0-3 min. After 3 min the mobile phase composition was changed to 75:25 ratio. The retention time of ketoprofen was 1.69 min. The linear concentration of ketoprofen was established in the range of 0.1-25 µg/ml and LOQ for ketoprofen was 0.03 µg/ml. For nadolol, the used column was HSS-T3 1.8 µm (2.1×50 mm) (Waters, USA) at 30° C. The flow rate was 0.5 ml/min and the injection volume 5 µl. The nadolol detection was performed at 215 nm wavelength. During the gradient run the mobile phase consisted of a mixture of acetonitrile and 15 mM phosphate buffer pH 2 in 10:90 ratio at 0-3 min. After 3 min the mobile phase composition was changed to 50:50 ratio. The retention time of nadolol was 0.92 min. The linear concentration of nadolol was established in the range of 0.1-50 µg/ml and LOQ for nadolol was 0.1 µg/ml.

FITC-dextran quantification was performed by fluorescence intensity measurements with an automated multimode plate reader Varioskan Flash (Thermo Fisher Scientific, Finland). 200 µl of samples were pipetted into wells of 96-well OptiPlate plates (PerkinElmer, Finland). Excitation wavelength 490 nm, emission wavelength 520 nm and 12 nm bandwidth were used. The established linear range for FITC-dextran calibration curves was 0.005-0.15 µg/ml with squared correlation coefficients above 0.99 (R>0.99).

Metronidazole and lysozyme quantification was performed by spectrophotometric analysis with Cary 100 UV-Vis spectrophotometer (Varian Inc., USA). For metronidazole, absorbance was measured in 1 cm cell at 320 nm with 12 nm bandwidth against blank. The established linear range for metronidazole calibration curve was 3-35 µg/ml with squared correlation coefficient above 0.99 (R>0.99). For lysozyme, absorbance was measured in 1 cm cell at 280 nm with 12 nm bandwidth against blank. The established linear range for lysozyme calibration curve was 1-17 µg/ml with squared correlation coefficient above 0.99 (R>0.99).

BSA quantification was performed by colorimetric Bio-Rad protein assay, which is based on Bradford dye-binding method. Shortly, 150 µl of each BSA standard sample and BSA sample was pipetted in triplicate into separate microtiter well plates and 50 µl of diluted Bradford dye reagent was added. Sample and reagent were mixed thoroughly with a multi-channel pipet and incubated for 20 minutes at room temperature before absorbance measurement. Absorbance was measured with a well plate reader Varioskan Flash ((Thermo Fisher Scientific, Finland) at 470 nm and 595 nm with 5 nm bandwidth. The established linear range for BSA calibration curves was 1-40 µg/ml with squared correlation coefficients above 0.99 (R>0.99). Linearization of the assay was used to improve accuracy and sensitivity.

Thermogravimetry Analysis (TGA)

The results from thermogravimetry analysis are presented in Table 5.

TABLE 5

Thermogravimetry analysis of different NFC hydrogel formulations. Residual moisture content of the freeze dried aerogels was determined as a mass loss (%) of evaporated water.

| Formulation | Mass change (%) |
| --- | --- |
| NFC 3.2% | 6.77 |
| NFC 3%/PEG6000 1%/TRE 0.3% | 4.11 |
| KETO 3.4%/NFC 3%/PEG6000 1%/TRE 0.3% | 1.96 |
| MZ 2%/NFC 3%/PEG6000 1%/TRE 0.3% | 2.42 |
| NAD 1.7%/NFC 3%/PEG6000 1%/TRE 0.3% | 2.9 |
| BSA 1%/NFC 3%/PEG6000 1%/TRE 0.3% | 4.79 |
| NFC 6.8% | 7.48 |
| NFC 6.5%/PEG6000 1%/TRE 0.3% | 5.81 |
| KETO 3.4%/NFC 6.5%/PEG6000 1%/TRE 0.3% | 3.84 |

TABLE 5-continued

Thermogravimetry analysis of different NFC hydrogel formulations. Residual moisture content of the freeze dried aerogels was determined as a mass loss (%) of evaporated water.

| Formulation | Mass change (%) |
|---|---|
| MZ 2%/NFC 6.5%/PEG6000 1%/TRE 0.3% | 4.98 |
| NAD 1.7%/NFC 6.5%/PEG6000 1%/TRE 0.3% | 4.79 |
| BSA 1%/NFC 6.5%/PEG6000 1%/TRE 0.3% | 6.05 |

Differential Scanning Calorimetry

The results from differential scanning calorimetry are presented in Table 6.

TABLE 6

Differential scanning calorimetry analysis of different NFC hydrogel formulations.

| Formulation | Melting point ° C. NFC 3%/PEG6000 1%/ TRE 0.3% | Melting point ° C. NFC 6.5%/PEG6000 1%/ TRE 0.3% |
|---|---|---|
| NFC | 171.5 | 161 |
| NFC/PEG6000/ TRE | 53 (PEG6000), 170 (NFC + TRE) | 53 (PEG6000), 187 (NFC + TRE) |
| BSA | 49 (PEG6000), 176.3 (NFC + TRE) | 52 (PEG6000), 178.9 (NFC + TRE) |
| MZ | 49 (PEG6000) + 148.7 (MZ) | 143.5 (MZ), 186 (NFC + TRE) |
| NAD | 48.6 (PEG6000) + 127.3 (NAD)/ Tg 159.2 (TRE) | 128.3 (NAD), 186.4 (NFC + TRE)/ Tg 159.8 (TRE) |
| KETO | 37.9 (PEG6000) + 81 (KETO) | 84 (KETO) |

TABLE 7

Literature values of thermal properties for model compounds.

| Compound | Mp (° C.) | Tg (° C.) | Onset degradation temp $T_{d, N2}$ ° C. | Thermal degradation ° C. |
|---|---|---|---|---|
| TEMPO oxidized NFC | Removal of moisture 50-150 | — | 200 | 200-330 |
| Trehalose | 100 (dihydrate) and 215 (anhydrous) | 73-115 | 230 | 230 |
| PEG 6000 | 56, 59 and 63 | — | 257 | 257-403 |
| BSA | 73 | 90 | 220 | 220-500 |
| Metronidazole | 158-160 | — | 160 | 160-290 |
| Ketoprofen | 94-96 | −2 | 235 | 235-400 |
| Nadolol | 124-136 | — | 196.2 | 196-353 |

Rheological Measurements

Figure 4:
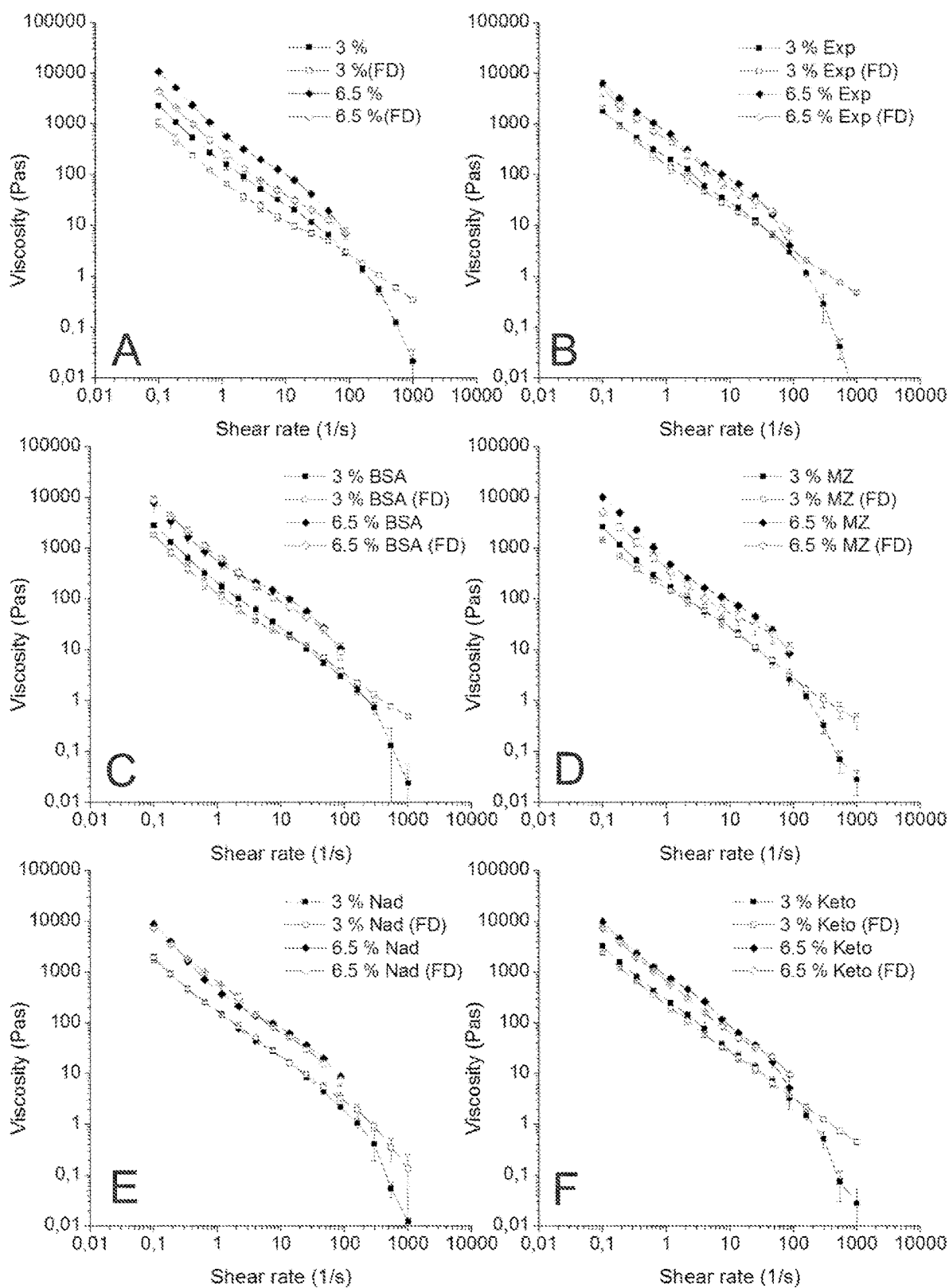
FIG. 4 shows shear rate viscosity of different formulations (3% and 6.5%) before and after (FD) freeze drying: A) with no excipients, B) with excipients (PEG and trehalose), C) with BSA and excipients, D) with metronidazole and excipients, E) with nadolol and excipients, F) with ketoprofen and excipients.

The results from the rheological measurements are presented in the FIG. 4 (Shear rate viscosity of different formulations before and after freeze drying), and in FIG. 1 (The effect of NFC hydrogel concentration and freeze drying on the release of metronidazole, nadolol, ketoprofen, BSA, lysozyme and 4 kDa FITC-dextran. Formulations contained 3% NFC hydrogel combined with metronidazole, nadolol, ketoprofen, BSA, lysozyme or 4 kDa FITC-dextran (a), 3% NFC hydrogel with PEG6000 and trehalose combined with metronidazole, nadolol, ketoprofen or BSA before and after freeze drying (b), 6.5% NFC hydrogel combined with metronidazole, nadolol, ketoprofen, BSA, lysozyme or 4 kDa FITC-dextran (c), 6.5% NFC hydrogel with PEG6000 and trehalose combined with metronidazole, nadolol, ketoprofen or BSA before and after freeze drying. Each curve is the mean±standard deviation of three analyses). The results are also presented in tables 8 and 9.

Both grades of NFC showed about 2.5 times higher viscosities than their respective rehydrated samples at shear rates ranging 0.1-40 (1/s). The presence of excipients reduced the gap between the curves to about 1.3 by increasing the viscosity of the freeze dried samples and lowering the plain hydrogel viscosities, more notably for the 6.5% hydrogels. The addition of model compounds did not significantly alter the viscosity curves when compared to the NFC hydrogels containing excipients before and after freeze drying. Therefore, the viscosity lowering effect of freeze drying was reduced (i.e. the stabilization with excipients was not lost). For BSA and MZ however, the gap between the viscosity curves was slightly wider prior to and after freeze drying than with the NFC hydrogels containing only excipients, for NAD and KETO, the gap was narrower. All samples expressed a steady decrease in viscosity with increasing shear rate. Freeze drying did not have an effect on shear thinning after rehydration, and the results indicate structural similarities before and after freeze drying processes.

TABLE 8

Physicochemical properties of model compounds.

| Compound | Molecular weight (g/mol) | Solubility in aqueous media (mg/ml) | pKa/pI | Charge at pH 7.0 | Hydro dynamic diameter (nm) |
|---|---|---|---|---|---|
| Ketoprofen | 254 | 0.107 (25° C.), 6.36 (pH 7) | 4.06 | − | — |
| Nadolol | 309 | 8.3 (25° C.), 8.3 (pH 7) | 9.28 | + | — |
| Metronidazole | 171 | 10.5 (25° C.), 10.5 (pH 7) | 2.38 | ø | — |
| BSA | $6.65 \times 10^4$ | 40 | 4.6-4.8 | − | ~7 |
| Lysozyme | $1.47 \times 10^4$ | >10 | 11.1 | + | ~3.7 |
| FITC-dextran | 4000 | 50 | | ø | ~2.8 |

TABLE 9

Diffusion coefficients for model compounds in different NFC hydrogels.
Values are presented for 3% and 6.5% NFC hydrogels with and
without excipients. Freeze dried formulations with excipients
were dispersed prior to diffusion studies.

| Compound* | Diffusion coefficients for model compounds in different NFC hydrogels ($10^{-8}$ cm$^2$/s) | | | | | |
|---|---|---|---|---|---|---|
| | 3% NFC | 3% NFC/exp | FD 3% NFC/exp | 6.5% NFC | 6.5% NFC/exp | FD 6.5% NFC/exp |
| Ketoprofen (−) | 152.62 | 147.15 | 129.97 | 141.86 | 141.20 | 124.44 |
| Nadolol (+) | 286.24 | 292.92 | 296.36 | 230.62 | 245.04 | 267.21 |
| Metronidazole (ø) | 716.99 | 657.41 | 699.10 | 617.51 | 617.16 | 660.18 |
| BSA (−) | 9.28 (±2.46) | 22.72 (±1.04) | 21.62 (±2.13) | 9.06 (±1.16) | 16.07 (±1.38) | 8.23 (±1.02) |
| Lysozyme (+) | 3.53 (±0.31) | nd | nd | 1.75 (±0.15) | nd | nd |
| 4 kDa FITC-dextran (ø) | 59.44 (±11.23) | nd | nd | 40.01 (±4.84) | nd | nd |

*Charge of compounds at pH 7.4 in parenthesis.
Abbreviation "exp" refers to PEG6000 and trehalose that were used as excipients.

Charge of the small molecules did not significantly affect the diffusion coefficients. Uncharged metronidazole had highest diffusion coefficients through all tested NFC hydrogel formulations. The NFC hydrogel concentration had an impact on the diffusion of small molecules as diffusion through 3% NFC was faster than from the 6.5% NFC hydrogel. Freeze drying of these formulations had only a minimal impact on the drug release profiles. For larger molecules significantly lower diffusion constant values were observed as opposed to small molecules. Molecular weight affects the diffusion through NFC hydrogel and the different fiber concentrations in the hydrogels provided a significant control for the diffusion. For 4 kDa, the diffusion rate was 1.5 times faster through 3% NFC hydrogel that 6.5% NFC hydrogel. Similarly it was observed that the diffusion of 14.7 kDa lysozyme was 2 times faster from the 3% NFC hydrogel than 6.5% hydrogel. Additionally, the cationic charge of lysozyme prolonged the diffusion through anionic NFC fiber network. This was most likely attributed to the electrostatic interactions. For 66.5 kDa BSA the diffusion coefficient were similar in 3% and 6.5% NFC hydrogels. This was most likely attributed to the larger size of BSA and indicated that the diffusion of large proteins through hydrogel is limited due to their size in a greater extent in addition to the fiber content in the hydrogel. The diffusion of the anionic 66.5 kDa BSA was not as limited as for 14.7 kDa lysozyme, but the release of BSA was still slower than for 4 kDa FITC-dextran. Therefore, it was found out that the diffusion of large molecules through NFC hydrogel is affected by the size as well as charge.

BSA was selected to be used as a model protein compound for the freeze drying. The diffusion coefficients of BSA were affected by the addition of PEG6000 and trehalose as well as freeze drying. The addition of the excipients decreased slightly the viscosity of the hydrogels which may have attributed to the higher diffusion constants as opposed to hydrogels without the excipients. The freeze drying of 3% NFC hydrogel did not significantly alter the release of BSA. By contrast, the diffusion was approximately 2 times slower from the freeze dried 6.5% NFC hydrogel after freeze drying. NFC is known to undergo irreversible hornification upon dehydration. The structure of the NFC fibers may have been slightly modified during freeze drying to an extent that affects the diffusion of large molecules such as BSA. This phenomena was not observed for any other model compound. It was found out that the release properties of the model compounds below 66.5 kDa were preserved during freeze drying.

The invention claimed is:

1. A freeze-dried medical aerogel comprising:
   nanofibrillar cellulose,
   a single active pharmaceutical ingredient selected from the group consisting of antibiotics, pain relievers; nicotine; opioids; nitroglycerin; scopolamine; clonidine; antidepressants; ADHD medication; vitamins; 5-hydroxytryptophan; Alzheimer's medication; acne medication; antipsoriatics, glucocorticoids; antiandrogens, antiestrogens, antimicrobial agents; anesthetics; analgesics; anti-inflammatory compounds or agents; antihistamines; beta-blockers; immunomodulators; and medication for treating diseases or disorders of skin,
   polyethylene glycol, and
   trehalose,
   wherein the moisture content of the aerogel is 10% (w/w) or less, and
   wherein the nanofibrillar cellulose, the polyethylene glycol and the trehalose are present in the aerogel in a weight ratio of nanofibrillar cellulose:polyethylene glycol:trehalose of 9-22:2-6:1.

2. The freeze-dried medical aerogel of claim 1, wherein the content of the active pharmaceutical ingredient in the aerogel is in the range of 0.1-65% (w/w).

3. The freeze-dried medical aerogel of claim 1, wherein the weight ratio of nanofibrillar cellulose:polyethylene glycol:trehalose is 9.5-20:2-4:1.

4. The freeze-dried medical aerogel of the claim 1, wherein the nanofibrillar cellulose prior to incorporation into the aerogel provides a Brookfield viscosity of at least 2000 mPa·s, measured at 20° C±1° C., at a consistency of 0.8% (w/w) and at 10 rpm.

5. The freeze-dried medical aerogel of the claim 1, wherein the nanofibrillar cellulose is selected from anionically modified nanofibrillar cellulose, cationically modified nanofibrillar cellulose and unmodified nanofibrillar cellulose, and TEMPO oxidized nanofibrillar cellulose.

6. The freeze-dried medical aerogel of claim 1, wherein the active pharmaceutical ingredient is selected from metronidazole, nadolol, ketoprofen, lidocaine, fentanyl, buprenorphine, selegiline, methylphenidate, rivastigmine, hydrocortisone, bifluranol, cyoctol, cyproterone, delmadinone acetate, flutimide, nilutamide, oxendolone, ethamoxytriphetol, tamoxifen, and toremifene.

7. The freeze-dried medical aerogel of claim 1, obtained with a method comprising:
   comprising
   providing a hydrogel comprising nanofibrillar cellulose,
   providing polyethylene glycol,
   providing trehalose,
   mixing the hydrogel, the polyethylene glycol and the trehalose to obtain a mixture, and
   freeze drying the mixture to obtain an aerogel comprising nanofibrillar cellulose.

8. The freeze-dried medical aerogel of claim 1, wherein the nanofibrillar cellulose is the only polymeric gel-forming material in the aerogel.

9. The freeze-dried medical aerogel of claim 1, wherein the nanofibrillar cellulose has a length exceeding 1 μm and a diameter smaller than 200 nm.

10. The freeze-dried medical aerogel of claim 1, wherein the nanofibrillar cellulose has a number average diameter of a fibril in the range of 1-100 nm.

11. The freeze-dried medical aerogel of claim 1, wherein the nanofibrillar cellulose prior to incorporation in the aerogel provides a zero shear viscosity in the range of 1000-100000 Pa·s and a yield stress in the range of 1-50 Pa, determined by rotational rheometer at a consistency of 0.5% (w/w) by weight in aqueous medium.

\* \* \* \* \*